United States Patent
Marks et al.

(10) Patent No.: US 11,396,657 B2
(45) Date of Patent: Jul. 26, 2022

(54) PLANTS HAVING INCREASED OIL QUALITY

(71) Applicants: Regents of the University of Minnesota, Minneapolis, MN (US); The Board of Trustees of Illinois State University, Normal, IL (US)

(72) Inventors: Michael David Marks, Roseville, MN (US); John C. Sedbrook, Bloomington, IL (US); Donald L. Wyse, Wyoming, MN (US); Kevin Dorn, Roseville, MN (US)

(73) Assignees: Regents of the University of Minnesota, Minneapolis, MN (US); The Board of Trustees of Illinois State University, Normal, IL (US)

( * ) Notice: Subject to any disclaimer, the term of this patent is extended or adjusted under 35 U.S.C. 154(b) by 0 days.

(21) Appl. No.: 16/480,881

(22) PCT Filed: Jan. 26, 2018

(86) PCT No.: PCT/US2018/015536
§ 371 (c)(1),
(2) Date: Jul. 25, 2019

(87) PCT Pub. No.: WO2018/140782
PCT Pub. Date: Aug. 2, 2018

(65) Prior Publication Data
US 2020/0131523 A1  Apr. 30, 2020

Related U.S. Application Data

(60) Provisional application No. 62/451,467, filed on Jan. 27, 2017.

(51) Int. Cl.
| | | |
|---|---|---|
| *C12N 15/82* | (2006.01) | |
| *C12N 9/10* | (2006.01) | |
| *A01H 5/10* | (2018.01) | |
| *A01H 6/20* | (2018.01) | |

(52) U.S. Cl.
CPC .......... *C12N 15/8247* (2013.01); *A01H 5/10* (2013.01); *A01H 6/20* (2018.05); *C12N 9/1085* (2013.01); *C12N 15/8213* (2013.01); *C12Y 205/01* (2013.01)

(58) Field of Classification Search
None
See application file for complete search history.

(56) References Cited

U.S. PATENT DOCUMENTS

| | | |
|---|---|---|
| 2008/0160530 A1 | 7/2008 | Li |
| 2015/0143573 A1 | 5/2015 | Denolf et al. |
| 2017/0051299 A1 | 2/2017 | Fabijanski et al. |
| 2019/0053457 A1 | 2/2019 | Marks et al. |
| 2019/0053458 A1 | 2/2019 | Marks et al. |
| 2020/0308596 A1 | 10/2020 | Marks et al. |
| 2020/0370062 A1 | 11/2020 | Marks et al. |

FOREIGN PATENT DOCUMENTS

| | | | |
|---|---|---|---|
| WO | WO 2000/036114 | 6/2000 | |
| WO | WO 2006/052912 | 5/2006 | |
| WO | WO 2013/112578 | 8/2013 | |
| WO | WO-2013112578 A1 * | 8/2013 | ......... C12N 15/8247 |
| WO | WO 2017/004375 | 1/2017 | |
| WO | WO 2017/117633 | 7/2017 | |
| WO | WO 2018/140782 | 8/2018 | |

OTHER PUBLICATIONS

Belide et al. (Frontiers in Plant Science, vol. 3, Jan. 1, 2012).*
Roscoe et al. (FEBS Letters., 492:107-111; 2001).*
Belide et al. (Frontiers in Plant Science, 3, pp. 1-6; Jul. 2012).*
Xi et al. (Molecular Plant., 6(6):1975-1983; Published Nov. 2013).*
Sedbrook et al. (Plant Science, 227:122-132, 2014).*
Zeng et al. (Plant cell, 26:2648-2659, Jun. 2014).*
Britt, "From stinkweed to oilseed," Nat. Food, 1:24-25, Jan. 2020.
Chopra et al., "Identification and stacking of crucial traits required for the domestication of pennycress," Nat. Food, 1:84-91, Jan. 2020.
Claver et al., "Identification of target genes and processes involved in erucic acid accumulation during seed development in the biodiesel feedstock Pennycress (*Thlaspi arvense* L.)," Journal of plant physiology, 208:7-16, Jan. 2017.
Downey and Craig, "Genetic control of fatty acid biosynthesis in rapeseed (*Brassica napus* L.)," Journal of the American Oil Chemists' Society, Jul;41(7):475-8, Jul. 1964.
Fourmann et al., "The two genes homologous to *Arabidopsis* FAE1 co-segregate with the two loci governing erucic acid content in *Brassica napus*," Theor. Appl. Genet., 96(6-7):852-8, May 1998.
James et al., "Directed Tagging of the *Arabidopsis* Fatty Acid Elongation1 (FAE1) Gene with the Maize Transposon Activator," The Plant Cell, 7:309-319, Mar. 1995.
Javidfar and Cheng, "Single locus, multiallelic inheritance of erucic acid content and linkage mapping of FAE1 gene in yellow mustard," Crop Science, 53(3):825-32, May 2013.
Baud et al., "Physiological and developmental regulation of seed oil production," Prog Lipid Res., 49(3):235-49, Jul. 2010.
Belide et al., "Modification of seed oil composition in *Arabidopsis* by artificial microRNA-mediated gene silencing," Frontiers in plant science, 3:168, Jul. 2012.

(Continued)

*Primary Examiner* — Vinod Kumar
(74) *Attorney, Agent, or Firm* — Fish & Richardson P.C.

(57) ABSTRACT

This document provides materials and methods for generating oilseed (e.g., pennycress) plants that having low levels of erucic acid. For example, oilseed plants having reduced expression levels of one or more polypeptides involved in erucic acid metabolism (e.g., fatty acid elongase 1 (FAE1)), as well as materials and methods for making and using oilseed plants having low levels of erucic acid are provided.

16 Claims, 9 Drawing Sheets
Specification includes a Sequence Listing.

(56) References Cited

OTHER PUBLICATIONS

Bell, "Factors affecting the nutritional value of canola meal: a review," Canadian Journal of Animal Science, 73(4):679-697, Dec. 1993.

Bligh et al., "A rapid method of total lipid extraction and purification," Canadian Journal of Biochemistry and Physiology, 37(8):911-917, Aug. 1959.

Boateng et al., "Producing stable pyrolysis liquids from the oil-seed presscakes of mustard family plants: Pennycress (*Thlaspi arvense* L.) and Camelina (*Camelina sativa*)," Energy & Fuels, 24(12):6624-6632, Nov. 2010.

Calver et al., "Identification of target genes and processes involved in erucic acid accumulation during seed development in the biodiesel feedstock Pennycress (*Thlaspi arvense* L.)," J. Plant Physiol., 208:7-16, Jan. 2017.

Chopra et al., "The adaptable use of *Brassica* NIRS calibration equations to identify pennycress variants to facilitate the rapid domestication of a new winter oilseed crop," Industrial Crops and Products, 128:55-61, Feb. 2019.

Chopra et al., "Transcriptome profiling and validation of gene based single nucleotide polymorphisms (SNPs) in sorghum genotypes with contrasting responses to cold stress," BMC Genomics, 16(1):1040, Dec. 2015.

Chopra et al., "Translational genomics using *Arabidopsis* as a model enables the characterization of pennycress genes through forward and reverse genetics," The Plant Journal, 96(6):1093-1105, Dec. 2018.

Crevillén et al., "Epigenetic reprogramming that prevents transgenerational inheritance of the vernalized state," Nature, 515(7528):587-90, Nov. 2014.

Dorn et al., "De novo assembly of the pennycress (*Thlaspi arvense*) transcriptome provides tools for the development of a winter cover crop and biodiesel feedstock," The Plant Journal, 75(6):1028-38, Sep. 2013.

Fauser et al., "Both CRISPR/C as-based nucleases and nickases can be used efficiently for genome engineering in *Arabidopsis thaliana*," Plant J., 79(2):348-359, Jul. 2014.

Ferrándiz et al., "Negative regulation of the SHATTERPROOF genes by FRUITFULL during *Arabidopsis* fruit development," Science, 289(5478):436-438, Jul. 2000.

Girin et al., "*Brassicaceae* INDEHISCENT genes specify valve margin cell fate and repress replum formation," Plant J., 63(2):329-338, Jul. 2010.

Golebiewski et al., "Near infrared reflectance spectroscopy of oil in intact canola seed (*Brassica napus* L.). II. Association between principal components and oil content," Journal of near Infrared Spectroscopy, 13(5):255-264, Oct. 2005.

Han et al., "Functional characterization of beta-ketoacyl-CoA synthase genes from *Brassica napus* L," Plant molecular biology, 46(2):229-39, May 2001.

International Preliminary Report on Patentability in International Application No. PCT/US2018/015536 dated Aug. 8, 2019, 7 pages.

International Search Report & Written Opinion in International Application No. PCT/US2018/015536 dated Apr. 13, 2018, 16 pages.

Kim et al., "Toward production of jet fuel functionality in oilseeds: identification of FatB acyl-acyl carrier protein thioesterases and evaluation of combinatorial expression strategies in Camelina seeds," Journal of Experimental Botany, 66(14):4251-4265, May 2015.

Liljegren et al., "SHATTERPROOF MADS-box genes control seed dispersal in *Arabidopsis*," Nature, 404(6779):766-770, Apr. 2000.

McGinn et al., "Molecular tools enabling pennycress (*Thlaspi arvense*) as a modelplant and oilseed cash cover crop," Plant Biotechnology Journal, 17(4):776-788, Apr. 2019.

Montero de Espinosa et al., "Plant oils: The perfect renewable resource for polymer science?!" European Polymer Journal, 47(5):837-852, May 2011.

Moser et al., "Composition and physical properties of cress (*Lepidium sativum* L.) and field pennycress (*Thlaspi arvense* L.) oils," Industrial Crops and Products, 30(2):199-205, Sep. 2009.

Moser et al., "Production and evaluation of biodiesel from field pennycress (*Thlaspi arvense* L.) oil," Energy & Fuels, 23(8):4149-4155, Jul. 2009.

Phippen et al., "Soybean seed yield and quality as a response to field pennycress residue," Crop Science, 52(6):2767-2773, Nov. 2012.

Riu et al., "[Detection of erucic acid and glucosinolate in intact rapeseed by near-infrared diffuse reflectance spectroscopy]," Spectroscopy and Spectral Analysis, Dec. 2006, 26(12):2190-2192, (with English abstract).

Roeder et al., "The role of the REPLUMLESS homeodomain protein in patterning the *Arabidopsis* fruit," Curr. Biol., 13(18):1630-1635, Sep. 2003.

Rosas et al., "One-step, codominant detection of imidazolinone resistance mutations in weedy rice (*Oryza sativa* L.)," Electron. J. Biotechnol., 17:95-101, Mar. 2014.

Roscoe et al., "Mutations in the fatty acid elongation 1 gene are associated with a loss of β-ketoacyl-CoA synthase activity in low erucic acid rapeseed," FEBS letters, 492(1-2):107-11, Mar. 2001.

Sedbrook et al., "New approaches to facilitate rapid domestication of a wild plant to an oilseed crop: example pennycress (*Thlaspi arvense* L.)," Plant Sci., 227:122-32, Oct. 2014.

Sedbrook et al., "New approaches to facilitate rapid domestication of a wild plant to an oilseed crop: example pennycress (*Thlaspi arvense* L.)," Plant Science, 227:122-132, Oct. 2014.

Sidhu et al., "Diode Array Near Infrared Spectrometer Calibrations for Composition Analysis of Single Plant Canola (*Brassica napus*) Seed," Applied Engineering in Agriculture, 30(1):69-76, Jan. 2014.

Steinert et al., "Highly efficient heritable plant genome engineering using Cas9 orthologues from *Streptococcus thermophilus* and *Staphylococcus aureus*," Plant J., 84:1295-305, Dec. 2015.

Warwick et al., "The biology of Canadian weeds. 9. *Thlaspi arvense* L.(updated)," Canadian Journal of Plant Science, 82(4):803-823, Oct. 2002.

Wu et al., "Zero erucic acid trait of rapeseed (*Brassica napus* L.) results from a deletion of four base pairs in the fatty acid elongase 1 gene," Theoretical and applied genetics, 116(4):491-9, Feb. 2008.

Xin et al., "Mid-infrared spectral characteristics of lipid molecular structures in *Brassica carinata* seeds: relationship to oil content, fatty acid and glucosinolate profiles, polyphenols, and condensed tannins," J. Agric. Food Chem., 62(32):7977-7988, Aug. 2014.

U.S. Appl. No. 16/104,318, filed Aug. 17, 2018, Michael David Marks, Published.

U.S. Appl. No. 16/104,478, filed Aug. 17, 2018, Michael David Marks, Published.

Kano-Murakami et al., "A rice homeotic gene, OSH1, causes unusual phenotypes in transgenic tobacco," FEBS letters, 334(3):365-8, Nov. 1993.

Yu et al., "Modulation of brassinosteroid-regulated gene expression by Jumonji domain-containing proteins ELF6 and REF6 in *Arabidopsis*," Proceedings of the National Academy of Sciences, 105(21):7618-23, May 2008.

Blacklock et al., "Substrate specificity of *Arabidopsis* 3-ketoacyl-CoA synthases," Biochem. Biohpys. Res. Communications, Jun. 5, 2006, 346(2):583-590.

GenBank Accession No. KT223025.1, "Thlaspi arvense cultivar French 3-ketoacyl-CoA synthase (FAE1) mRNA, complete cds," Nov. 29, 2015, 2 pages.

Joubes et al., "The VLCFA elongase gene family in *Arabidopsis thaliana*: phylogenetic analysis, 3D modelling and expression profiting," Plant Mol. Biology, May 9, 2008, 67(5):547-566.

Millar et al., "Very-long-chain fatty acid biosynthesis is controlled through the expression and specificity of the condensing enzyme," Plant Journal, Jul. 1997, 12(1):121-131.

Morineau et al., "Dual Fatty Acid Elongase Complex Interactions in *Arabidopsis*," PLoS One, Sep. 1, 2016, 11(9):e0160631, 20 pages.

Wang et al., "A functional genomics resource for *Brassica napus*: development of an EMS mutagenized population and discovery of FAE1 point mutations by TILLING," New Phytologist, Dec. 2008, 180(4):751-765.

U.S. Appl. No. 16/831,145, filed Mar. 26, 2020, Michael David Marks, Published.

(56) References Cited

OTHER PUBLICATIONS

U.S. Appl. No. 16/969,434, filed Aug. 12, 2020, Michael David Marks, Published.
Batsale et al., "Biosynthesis and Functions of Very-Long-Chain Fatty Acids in the Responses of Plants to Abiotic and Biotic Stresses," Cells, May 21, 2021, 10:1284, 26 pages.
Claver et al., "Functional analysis of β-ketoacyl-CoA synthase from biofuel feedstock Thlaspi arvense reveals differences in the triacylglycerol biosynthetic pathway among *Brassicaceae*," Plant Mol. Biology, 104(3):283-296, Aug. 1, 2020.
Dorn et al., "A draft genome of field pennycress (*Thlaspi arvense*) provides tools for the domestication of a new winter biofuel crop," DNA Research, Apr. 2015, 22(2):121-131.
ENA Accession No. PRJEB46635, "Chromosome-level *Thlaspi arvense* genome provides new tools for translational research and for a newly domesticated cash cover crop of the cooler climates," dated Aug. 2, 2021, 2 pages.
GenBank Accession No. AAC49186.1, "beta-ketoacyl-CoA synthase [Simmondsia chinensis]," dated Oct. 31, 1995, 2 pages.
GenBank Accession No. AZNP01000000.1, "*Thlaspi arvense* cultivar MN106, whole genome shotgun sequencing project," dated Mar. 19, 2015, 1 page.
GenBank Accession No. NP_195178.1, "3-ketoacyl-CoA synthase 18 [*Arabidopsis thaliana*]," dated Jan. 22, 2014, 2 pages.
Geng et al., "Genomic analysis of field pennycress (*Thlaspi arvense*) provides insights into mechanisms of adaptation to high elevation," BMC Biology, Jul. 22, 2021, 19:143, 14 pages.
Gigolashvili et al., "The R2R3-MYB transcription factor HAG1/MYB28 is a regulator of methionine-derived glucosinolate biosynthesis in *Arabidopsis thaliana*," Plant Journal, 51(2):247-261, Jul. 2007.
Haslam et al., "Extending the story of very-long-chain fatty acid elongation," Plant Science, 210:93-107, Sep. 2013.
Kafri et al., "The regulatory utilization of genetic redundancy through responsive backup circuits," Proc. Nat. Acad. Sci. USA, 103(31):11653-11658, Aug. 2006.
Lassner et al., "A jojoba beta-Ketoacyl-CoA synthase cDNA complements the canola fatty acid elongation mutation in transgenic plants," Plant Cell, 8(2):281-292, Feb. 1996.
Nunn et al., "Chromosome-level *Thlaspi arvense* genome provides new tools for translational research and for a newly domesticated cash cover crop of the cooler climates," bioRxiv, Aug. 1, 2021, 48 pages.

Shen et al., "Resistance gene candidates identified by PCR with degenerate oligonucleotide primers map to clusters of resistance genes in lettuce," Mol. Plant Microbe Interactions, 11(8):815-823, Aug. 1998.
Tresch et al., "Inhibition of saturated very-long-chain fatty acid biosynthesis by mefluidide and perfluidone, selective inhibitors of 3-ketoacyl-CoA synthases," Phytochemistry, Apr. 2012, 76:162-171.
Yang et al., "Comprehensive analysis of KCS gene family in Citrinae reveals the involvement of CsKCS2 and CsKCS11 in fruit cuticular wax synthesis at ripening," Plant Science, Sep. 2021, 310:110972, 11 pages.
Blande et al. (GenBank Sequence Accession No. GEVK01020461.1, Published Nov. 4, 2016).
Bai et al., "The Biochemistry of Headgroup Exchange During Triacylglycerol Synthesis in Canola," The Plant Journal, 103(1):83-94, Jan. 2020.
Katavic et al., "Alteration of Seed Fatty Acid Composition by an Ethyl Methanesulfonate-induced Mutation in *Arabidopsis thaliana* Affecting Diacylglycerol Acyltransferase Activity," Plant Physiology, May 1995, 108(1):399-409.
Lu et al., "*Arabidopsis* Mutants Deficient in Diacylglycerol Acyltransferase Display Increased Sensitivity to Abscisic Acid, Sugars, and Osmotic Stress During Germination and Seedling Development," Plant Physiology, Jul. 2002, 129(3):1352-1358.
Lu et al., "Expression pattern of diacylglycerol acyltransferase-1, an enzyme involved in triacylglycerol biosynthesis, in *Arabidopsis thaliana*," Plant Mol. Biology, May 2003, 52(1):31-41.
Routaboul et al., "The TAG1 locus of *Arabidopsis* encodes for a diacylglycerol acyltransferase," Plant Physiol Biochemistry, Nov. 1999, 37(11):831-840.
Sanyal et al. "Stearic sunflower oil as a sustainable and healthy alternative to palm oil. A review," Agron. Sustain. Development, May 17, 2017, 37:18, 11 pages.
Van Gelderen et al, "An INDEHISCENT-Controlled Auxin Response Specifies the Separation Layer in Early *Arabidopsis* Fruit," Molecular Plant, Jun. 2016, 9:857-869.
Vogel et al., "Expression of the *Arabidopsis* WRINKLED 1 transcription factor leads to higher accumulation of palmitate in soybean seed," Plant Biotechnol. Journal, Jan. 17, 2019, 17(7):1369-1379.
Zarhloul et al., "Breeding high-stearic oilseed rape (*Brassica napus*) with high- and low-erucic background using optimised promoter-gene constructs," Mol. Breeding, Sep. 2006, 18(3):241-251.
Zou et al., "The *Arabidopsis thaliana* TAG1 mutant has a mutation in a diacylglycerol acyltransferase gene.," The Plant Journal, Sep. 1999, 19(6):645-653.

\* cited by examiner

A.

B.

C.

SEQUENCE LISTING

```
<160> NUMBER OF SEQ ID NOS: 19

<210> SEQ ID NO 1
<211> LENGTH: 1521
<212> TYPE: DNA
<213> ORGANISM: Thlaspi arvense

<400> SEQUENCE: 1
atgacgtccg ttaacgttaa gctcctttac cattacgtca tcaccaactt tttcaacctt      60
tgcttcttcc cgttagcggc gatcgttgcc ggaaaagcct ctcggcttac cacaaacgat     120
cttcaccact tctactattc ctatctccaa cacaacctaa taccatatc tctactcttt      180 gccttcaccg ttttcggttt ggctctctac atcgtaaccc ggcccaaacc ggtttacctc     240
gttgaccatt cctgctacct tccaccatcg catcttagaa gcagtatctc taaggtcatg     300
gatatcttct atcaagtaag attagccgat cctttacgga acgcggcaag cgatgattcg     360
tcctggcttg atttcttgag gaagattcag gagcggtctg gtctaggcga tgaaacccac     420
ggccccgagg gactgcttca ggtccctcca cggaagactt ttgccgcggc gcgtgaagaa     480
acagagcaag tgatcatcgg tgcgctcgaa aaactattcg agaacaccaa agttaaccct     540
aaagagattg gtatacttgt ggtgaactca agcatgttta atccgactcc ttcgctctcg     600
gcgatggttg ttaatacttt caagctccga agcaacatca gaagctttaa tcttggagga     660
atgggttgta gtgccggcgt tatagccatt gatctggcta aggacttgtt gcatgtccat     720
aaaaacactt atgctcttgt ggtgagcaca gagaacatca cttacaacat ttatgctggt     780
gataacagat ccatgatggt ttcgaattgc ttgttccgtg ttggtggggc cgcgattttg     840
ctctccaaca agccgaggga ccggagacgg tccaagtacc agctacttca cacggttcgg     900
acgcataccg gagctgacga caagtctttc cgatgtgtgc aacaagaaga cgacgagagc     960
ggtaaaaccg gggtgtgttt gtccaaggac ataaccggtg ttgccgggag aactgttcag    1020
aaaaacataa caacattggg tccgttggtt cttcctttta gcgagaaatt tctttttttc    1080
gttaccttca tcgccaagaa actctttaaa gacaagatca aacattacta cgtcccggat    1140
ttcaagcttg ctatcgacca tttttgtatt catgccggag gcagagccgt gatcgatgtg    1200
ctacagaaga acttaggtct attgccgatc gatgtggagg catctaggtc aacgttacat    1260
agatttggga acacttcgtc tagctcaatt tggtatgaat tggcgtacat agaggcaaaa    1320
ggaaggatga agagagggaa caaagtttgg cagattgctt tagggtcagg gtttaagtgt    1380
aatagtgcgg tttgggtggc tctacgcaat gtcaaggctt cgacaaatag tccttgggaa    1440
cattgcattg atagatatcc agatgcaatt gattctgatt cgggtaagtc agagactcgt    1500
gtccaaaacg gtcggtccta a                                              1521

<210> SEQ ID NO 2
<211> LENGTH: 506
<212> TYPE: PRT
<213> ORGANISM: Thlaspi arvense
```

<400> SEQUENCE: 2

```
Met Thr Ser Val Asn Val Lys Leu Leu Tyr His Tyr Val Ile Thr Asn
1               5                   10                  15

Phe Phe Asn Leu Cys Phe Phe Pro Leu Ala Ala Ile Val Ala Gly Lys
            20                  25                  30

Ala Ser Arg Leu Thr Thr Asn Asp Leu His His Phe Tyr Tyr Ser Tyr
        35                  40                  45

Leu Gln His Asn Leu Ile Thr Ile Ser Leu Leu Phe Ala Phe Thr Val
    50                  55                  60

Phe Gly Leu Ala Leu Tyr Ile Val Thr Arg Pro Lys Pro Val Tyr Leu
65                  70                  75                  80

Val Asp His Ser Cys Tyr Leu Pro Pro Ser His Leu Arg Ser Ser Ile
                85                  90                  95

Ser Lys Val Met Asp Ile Phe Tyr Gln Val Arg Leu Ala Asp Pro Leu
            100                 105                 110

Arg Asn Ala Ala Ser Asp Asp Ser Ser Trp Leu Asp Phe Leu Arg Lys
        115                 120                 125

Ile Gln Glu Arg Ser Gly Leu Gly Asp Glu Thr His Gly Pro Glu Gly
    130                 135                 140

Leu Leu Gln Val Pro Pro Arg Lys Thr Phe Ala Ala Arg Glu Glu
145                 150                 155                 160

Thr Glu Gln Val Ile Ile Gly Ala Leu Glu Lys Leu Phe Glu Asn Thr
                165                 170                 175

Lys Val Asn Pro Lys Glu Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Ile Arg Ser Phe Asn Leu Gly Gly Met Gly Cys Ser
    210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
            260                 265                 270

Arg Val Gly Gly Ala Ala Ile Leu Leu Ser Asn Lys Pro Arg Asp Arg
        275                 280                 285

Arg Arg Ser Lys Tyr Gln Leu Leu His Thr Val Arg Thr His Thr Gly
    290                 295                 300

Ala Asp Asp Lys Ser Phe Arg Cys Val Gln Gln Glu Asp Asp Glu Ser
305                 310                 315                 320

Gly Lys Thr Gly Val Cys Leu Ser Lys Asp Ile Thr Gly Val Ala Gly
                325                 330                 335

Arg Thr Val Gln Lys Asn Ile Thr Thr Leu Gly Pro Leu Val Leu Pro
            340                 345                 350

Phe Ser Glu Lys Phe Leu Phe Val Thr Phe Ile Ala Lys Lys Leu
        355                 360                 365

Phe Lys Asp Lys Ile Lys His Tyr Tyr Val Pro Asp Phe Lys Leu Ala
    370                 375                 380

Ile Asp His Phe Cys Ile His Ala Gly Gly Arg Ala Val Ile Asp Val
385                 390                 395                 400

Leu Gln Lys Asn Leu Gly Leu Leu Pro Ile Asp Val Glu Ala Ser Arg
```

```
                405                 410                 415
Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Arg Gly Asn Lys
            435                 440                 445

Val Trp Gln Ile Ala Leu Gly Ser Gly Phe Lys Cys Asn Ser Ala Val
450                 455                 460

Trp Val Ala Leu Arg Asn Val Lys Ala Ser Thr Asn Ser Pro Trp Glu
465                 470                 475                 480

His Cys Ile Asp Arg Tyr Pro Asp Ala Ile Asp Ser Asp Ser Gly Lys
                485                 490                 495

Ser Glu Thr Arg Val Gln Asn Gly Arg Ser
            500                 505

<210> SEQ ID NO 3
<211> LENGTH: 1517
<212> TYPE: DNA
<213> ORGANISM: Artificial Sequence
<220> FEATURE:
<223> OTHER INFORMATION: modified Thlaspi arvense FAE1 sequence

<400> SEQUENCE: 3
atgacgtccg ttaacgttaa gctcctttac cattacgtca tcaccaactt tttcaacctt      60
tgcttcttcc cgttagcggc gatcgttgcc ggaaaagcct ctcggcttac acaaacgat     120 cttcaccact tctactattc ctatctccaa cacaacctaa taaccatatc tctactcttt     180
gccttcaccg ttttcggttt ggctctctac atacccggcc caaaccggtt tacctcgttg     240
accattcctg ctaccttcca ccatcgcatc ttagaagcag tatctctaag gtcatggata     300
tcttctatca gtaagatta gccgatcctt tacggaacgc ggcaagcgat gattcgtcct     360
ggcttgattt cttgaggaag attcaggagc ggtctggtct aggcgatgaa acccacggcc     420
ccgagggact gcttcaggtc cctccacgga agacttttgc cgcggcgcgt gaagaaacag     480
agcaagtgat catcggtgcg ctcgaaaaac tattcgagaa caccaaagtt aaccctaaag     540
agattggtat acttgtggtg aactcaagca tgtttaatcc gactccttcg ctctcggcga     600
tggttgttaa ctttcaag ctccgaagca acatcagaag ctttaatctt ggaggaatgg     660
gttgtagtgc cggcgttata gccattgatc tggctaagga cttgttgcat gtccataaaa     720
acacttatgc tcttgtggtg agcacagaga acatcactta caacatttat gctggtgata     780
acagatccat gatggtttcg aattgcttgt tccgtgttgg tggggccgcg attttgctct     840
ccaacaagcc gagggaccgg agacggtcca agtaccagct acttcacacg ttcggacgc     900 ataccggagc tgacgacaag tcttttccgat gtgtgcaaca agaagacgac gagagcggta     960
aaaccggggt gtgtttgtcc aaggacataa ccggtgttgc cgggagaact gttcagaaaa    1020
acataacaac attgggtccg ttggttcttc cttttagcga gaatttctt ttttttcgtta    1080 ccttcatcgc caagaaactc tttaaagaca agatcaaaca ttactacgtc ccggatttca    1140
agcttgctat cgaccatttt tgtattcatg ccggaggcag agccgtgatc gatgtgctac    1200
agaagaactt aggtctattg ccgatcgatg tggaggcatc taggtcaacg ttacatagat    1260
ttgggaacac ttcgtctagc tcaatttggt atgaattggc gtacatagag gcaaaaggaa    1320
ggatgaagag agggaacaaa gtttggcaga ttgctttagg gtcagggttt aagtgtaata    1380
gtgcggtttg ggtggctcta cgcaatgtca aggcttcgac aaatagtcct ggaacatt    1440 gcattgatag atatccagat gcaattgatt ctgattcggg taagtcagag actcgtgtcc    1500
```
aaaacggtcg gtcctaa                                                        1517

<210> SEQ ID NO 4
<211> LENGTH: 104
<212> TYPE: PRT
<213> ORGANISM: Artificial Sequence
<220> FEATURE:
<223> OTHER INFORMATION: modified Thlaspi arvense FAE1 sequence

<400> SEQUENCE: 4

Met Thr Ser Val Asn Val Lys Leu Leu Tyr His Tyr Val Ile Thr Asn
1               5                   10                  15

Phe Phe Asn Leu Cys Phe Phe Pro Leu Ala Ala Ile Val Ala Gly Lys
            20                  25                  30

Ala Ser Arg Leu Thr Thr Asn Asp Leu His His Phe Tyr Tyr Ser Tyr
        35                  40                  45

Leu Gln His Asn Leu Ile Thr Ile Ser Leu Leu Phe Ala Phe Thr Val
    50                  55                  60

Phe Gly Leu Ala Leu Tyr Ile Pro Gly Pro Asn Arg Phe Thr Ser Leu
65                  70                  75                  80

Thr Ile Pro Ala Thr Phe His His Arg Ile Leu Glu Ala Val Ser Leu
                85                  90                  95

Arg Ser Trp Ile Ser Ser Ile Lys
            100

<210> SEQ ID NO 5
<211> LENGTH: 1522
<212> TYPE: DNA
<213> ORGANISM: Artificial Sequence
<220> FEATURE:
<223> OTHER INFORMATION: modified Thlaspi arvense FAE1 sequence

<400> SEQUENCE: 5
atgacgtccg ttaacgttaa gctcctttac cattacgtca tcaccaactt tttcaacctt        60
tgcttcttcc cgttagcggc gatcgttgcc ggaaaagcct ctcggcttac acaaacgat        120 cttcaccact tctactattc ctatctccaa cacaacctaa taccatatc tctactcttt        180 gccttcaccg ttttcggttt ggctctctac atcgtaaacc cggcccaaac cggtttacct       240
cgttgaccat tcctgctacc ttccaccatc gcatcttaga agcagtatct ctaaggtcat       300
ggatatcttc tatcaagtaa gattagccga tcctttacgg aacgcggcaa gcgatgattc       360
gtcctggctt gatttcttga ggaagattca ggagcggtct ggtctaggcg atgaaaccca       420 cggcccccgag ggactgcttc aggtccctcc acggaagact tttgccgcgg cgcgtgaaga      480
aacagagcaa gtgatcatcg gtgcgctcga aaaactattc gagaacacca agttaaccc       540 taaagagatt ggtatacttg tggtgaactc aagcatgttt aatccgactc cttcgctctc       600
ggcgatggtt gttaatactt tcaagctccg aagcaacatc agaagcttta atcttggagg       660
aatgggttgt agtgccggcg ttatagccat tgatctggct aaggacttgt tgcatgtcca       720
taaaaacact tatgctcttg tggtgagcac agagaacatc acttacaaca tttatgctgg       780
tgataacaga tccatgatgg tttcgaattg cttgttccgt gttggtgggg ccgcgatttt       840
gctctccaac aagccgaggg accggagacg gtccaagtac cagctacttc acacggttcg       900
gacgcatacc ggagctgacg acaagtcttt ccgatgtgtg caacaagaag acgacgagag       960
cggtaaaacc ggggtgtgtt tgtccaagga cataaccggt gttgccggga gaactgttca      1020 gaaaacata acaacattgg gtccgttggt tcttcctttt agcgagaaat ttctttttt       1080

```
cgttaccttc atcgccaaga aactctttaa agacaagatc aaacattact acgtcccgga    1140
tttcaagctt gctatcgacc attttgtat tcatgccgga ggcagagccg tgatcgatgt    1200
gctacagaag aacttaggtc tattgccgat cgatgtggag gcatctaggt caacgttaca    1260
tagatttggg aacacttcgt ctagctcaat ttggtatgaa ttggcgtaca tagaggcaaa    1320
aggaaggatg aagagaggga acaaagtttg gcagattgct ttagggtcag ggtttaagtg    1380
taatagtgcg gtttgggtgg ctctacgcaa tgtcaaggct cgacaaata gtccttggga    1440 acattgcatt gatagatatc cagatgcaat tgattctgat tcgggtaagt cagagactcg    1500
tgtccaaaac ggtcggtcct aa                                            1522

<210> SEQ ID NO 6
<211> LENGTH: 81
<212> TYPE: PRT
<213> ORGANISM: Artificial Sequence
<220> FEATURE:
<223> OTHER INFORMATION: modified Thlaspi arvense FAE1 sequence

<400> SEQUENCE: 6

Met Thr Ser Val Asn Val Lys Leu Leu Tyr His Tyr Val Ile Thr Asn
1               5                   10                  15

Phe Phe Asn Leu Cys Phe Phe Pro Leu Ala Ala Ile Val Ala Gly Lys
                20                  25                  30

Ala Ser Arg Leu Thr Thr Asn Asp Leu His His Phe Tyr Tyr Ser Tyr
            35                  40                  45

Leu Gln His Asn Leu Ile Thr Ile Ser Leu Leu Phe Ala Phe Thr Val
        50                  55                  60

Phe Gly Leu Ala Leu Tyr Ile Val Asn Pro Ala Gln Thr Gly Leu Pro
65                  70                  75                  80

Arg

<210> SEQ ID NO 7
<211> LENGTH: 1522
<212> TYPE: DNA
<213> ORGANISM: Artificial Sequence
<220> FEATURE:
<223> OTHER INFORMATION: modified Thlaspi arvense FAE1 sequence

<400> SEQUENCE: 7
atgacgtccg ttaacgttaa gctccttac cattacgtca tcaccaactt tttcaacctt     60
tgcttcttcc cgttagcggc gatcgttgcc ggaaaagcct ctcggcttac cacaaacgat    120
cttcaccact tctactattc ctatctccaa cacaacctaa taaccatatc tctactcttt    180
gccttcaccg tttcggtttt ggctctctac atcgtatacc cggcccaaac cggtttacct    240
cgttgaccat tcctgctacc ttccaccatc gcatcttaga agcagtatct ctaaggtcat    300
ggatatcttc tatcaagtaa gattagccga tcctttacgg aacgcggcaa gcgatgattc    360
gtcctggctt gatttcttga ggaagattca ggagcggtct ggtctaggcg atgaaaccca    420
cggccccgag ggactgcttc aggtccctcc acggaagact tttgccgcgg cgcgtgaaga    480
aacagagcaa gtgatcatcg gtgcgctcga aaaactattc gagaacacca agttaaccc     540 taaagagatt ggtatacttg tggtgaactc aagcatgttt aatccgactc cttcgctctc    600
ggcgatggtt gttaatactt tcaagctccg aagcaacatc agaagcttta atcttggagg    660
aatgggttgt agtgccggcg ttatagccat tgatctggct aaggacttgt tgcatgtcca    720
taaaaacact tatgctcttg tggtgagcac agagaacatc acttacaaca tttatgctgg    780
```

```
tgataacaga tccatgatgg tttcgaattg cttgttccgt gttggtgggg ccgcgatttt      840
gctctccaac aagccgaggg accggagacg gtccaagtac cagctacttc acacggttcg      900
gacgcatacc ggagctgacg acaagtcttt ccgatgtgtg caacaagaag acgacgagag      960
cggtaaaacc ggggtgtgtt tgtccaagga cataaccggt gttgccggga gaactgttca     1020
gaaaaacata caacattggg tccgttggt tcttcctttt agcgagaaat ttcttttttt     1080
cgttaccttc atcgccaaga aactctttaa agacaagatc aaacattact acgtcccgga     1140
tttcaagctt gctatcgacc atttttgtat tcatgccgga ggcagagccg tgatcgatgt     1200
gctacagaag aacttaggtc tattgccgat cgatgtggag gcatctaggt caacgttaca     1260
tagatttggg aacacttcgt ctagctcaat ttggtatgaa ttggcgtaca tagaggcaaa     1320
aggaaggatg aagagaggga acaaagtttg gcagattgct ttagggtcag ggtttaagtg     1380
taatagtgcg gtttgggtgg ctctacgcaa tgtcaaggct tcgacaaata gtccttggga     1440
acattgcatt gatagatatc cagatgcaat tgattctgat tcgggtaagt cagagactcg     1500
tgtccaaaac ggtcggtcct aa                                              1522
```

<210> SEQ ID NO 8
<211> LENGTH: 81
<212> TYPE: PRT
<213> ORGANISM: Artificial Sequence
<220> FEATURE:
<223> OTHER INFORMATION: modified Thlaspi arvense FAE1 sequence

<400> SEQUENCE: 8

```
Met Thr Ser Val Asn Val Lys Leu Leu Tyr His Tyr Val Ile Thr Asn
1               5                   10                  15

Phe Phe Asn Leu Cys Phe Phe Pro Leu Ala Ala Ile Val Ala Gly Lys
            20                  25                  30

Ala Ser Arg Leu Thr Thr Asn Asp Leu His His Phe Tyr Tyr Ser Tyr
        35                  40                  45

Leu Gln His Asn Leu Ile Thr Ile Ser Leu Leu Phe Ala Phe Thr Val
    50                  55                  60

Phe Gly Leu Ala Leu Tyr Ile Val Asn Pro Ala Gln Thr Gly Leu Pro
65                  70                  75                  80

Arg
```

<210> SEQ ID NO 9
<211> LENGTH: 1520
<212> TYPE: DNA
<213> ORGANISM: Artificial Sequence
<220> FEATURE:
<223> OTHER INFORMATION: modified Thlaspi arvense FAE1 sequence

<400> SEQUENCE: 9

```
atgacgtccg ttaacgttaa gctcctttac cattacgtca tcaccaactt tttcaacctt       60
tgcttcttcc cgttagcggc gatcgttgcc ggaaaagcct ctcggcttac cacaaacgat      120
cttcaccact tctactattc ctatctccaa cacaacctaa taccatatc tctactcttt      180 gccttcaccg ttttcggttt ggctctctac atcgtaccccg gccaaaaccg gtttacctcg      240
ttgaccattc ctgctaccttccaccatcgc atcttagaag cagtatctct aaggtcatgg      300
atatcttcta tcaagtaaga ttagccgatc ctttacggaa cgcggcaagc gatgattcgt      360
cctggcttga tttcttgagg aagattcagg agcggtctgg tctaggcgat gaaacccacg      420
gccccgaggg actgcttcag gtccctccac ggaagacttt tgccgcggcg cgtgaagaaa      480
```

```
cagagcaagt gatcatcggt gcgctcgaaa aactattcga gaacaccaaa gttaaccta      540 aagagattgg tatacttgtg gtgaactcaa gcatgtttaa tccgactcct tcgctctcgg     600
cgatggttgt taatactttc aagctccgaa gcaacatcag aagctttaat cttggaggaa    660
tgggttgtag tgccggcgtt atagccattg atctggctaa ggacttgttg catgtccata    720
aaaacactta tgctcttgtg gtgagcacag agaacatcac ttacaacatt tatgctggtg    780
ataacagatc catgatggtt tcgaattgct tgttccgtgt tggtggggcc gcgattttgc    840
tctccaacaa gccgagggac cggagacggt ccaagtacca gctacttcac acggttcgga    900
cgcataccgg agctgacgac aagtcttcc gatgtgtgca acaagaagac gacgagagcg     960
gtaaaaccgg ggtgtgtttg tccaaggaca taaccggtgt tgccgggaga actgttcaga   1020
aaaacataac aacattgggt ccgttggttc ttccttttag cgagaaattt ctttttttcg   1080
ttaccttcat cgccaagaaa ctctttaaag acaagatcaa acattactac gtcccggatt   1140
tcaagcttgc tatcgaccat ttttgtattc atgccggagg cagagccgtg atcgatgtgc   1200
tacagaagaa cttaggtcta ttgccgatcg atgtggaggc atctaggtca acgttacata   1260
gatttgggaa cacttcgtct agctcaattt ggtatgaatt ggcgtacata gaggcaaaag   1320
gaaggatgaa gagagggaac aaagtttggc agattgcttt agggtcaggg tttaagtgta   1380
atagtgcggt ttgggtggct ctacgcaatg tcaaggcttc gacaaatagt ccttgggaac   1440
attgcattga tagatatcca gatgcaattg attctgattc gggtaagtca gagactcgtg   1500
tccaaaacgg tcggtcctaa                                                1520
```

<210> SEQ ID NO 10
<211> LENGTH: 104
<212> TYPE: PRT
<213> ORGANISM: Artificial Sequence
<220> FEATURE:
<223> OTHER INFORMATION: modified Thlaspi arvense FAE1 sequence

<400> SEQUENCE: 10

```
Met Thr Ser Val Asn Val Lys Leu Leu Tyr His Tyr Val Ile Thr Asn
1               5                   10                  15

Phe Phe Asn Leu Cys Phe Phe Pro Leu Ala Ala Ile Val Ala Gly Lys
                20                  25                  30

Ala Ser Arg Leu Thr Thr Asn Asp Leu His His Phe Tyr Tyr Ser Tyr
            35                  40                  45

Leu Gln His Asn Leu Ile Thr Ile Ser Leu Leu Phe Ala Phe Thr Val
        50                  55                  60

Phe Gly Leu Ala Leu Tyr Ile Pro Gly Pro Asn Arg Phe Thr Ser Leu
65                  70                  75                  80

Thr Ile Pro Ala Thr Phe His His Arg Ile Leu Glu Ala Val Ser Leu
                85                  90                  95

Arg Ser Trp Ile Ser Ser Ile Lys
            100
```

<210> SEQ ID NO 11
<211> LENGTH: 1521
<212> TYPE: DNA
<213> ORGANISM: Artificial Sequence
<220> FEATURE:
<223> OTHER INFORMATION: modified Thlaspi arvense FAE1 sequence

<400> SEQUENCE: 11

```
atgacgtccg ttaacgttaa gctcctttac cattacgtca tcaccaactt tttcaacctt      60
```

```
tgcttcttcc cgttagcggc gatcgttgcc ggaaaagcct ctcggcttac cacaaacgat    120
cttcaccact tctactattc ctatctccaa cacaacctaa taaccatatc tctactcttt    180
gccttcaccg ttttcggttt ggctctctac atcgtaaccc ggcccaaacc ggtttacctc    240
gttgaccatt cctgctacct tccaccatcg catcttagaa gcagtatctc taaggtcatg    300
gatatcttct atcaagtaag attagccgat cctttacgga acgcggcaag cgatgattcg    360
tcctggcttg atttcttgag gaagattcag gagcggtctg gtctaggcga tgaaacccac    420
ggccccgagg gactgcttca ggtccctcca cggaagactt tgccgcggc gcgtgaagaa    480 acagagcaag tgatcatcgg tgcgctcgaa aaactattcg agaacaccaa agttaaccct    540
aaagagattg gtatacttgt ggtgaactca agcatgttta atccgactcc ttcgctctcg    600
gcgatggttg ttaatacttt caagctccga agcaacatca gaagctttaa tcttggagga    660
atgggttgta gtgccggcgt tatagccatt gatctggcta aggacttgtt gcatgtccat    720
aaaaacactt atgctcttgt ggtgagcaca gagaacatca cttacaacat ttatgctggt    780
gataacagat ccatgatggt ttcgaattgc ttgttccgtg ttggtggggc cgcgattttg    840
ctctccaaca agccgaggga ccggagacgt tccaagtacc agctacttca cacggttcgg    900
acgcataccg gagctgacga caagtctttc cgatgtgtgc aacaagaaga cgacgagagc    960
ggtaaaaccg gggtgtgttt gtccaaggac ataaccggtg ttgccgggag aactgtttag    1020
aaaaacataa caacattggg tccgttggtt cttccttta gcgagaaatt tctttttttc    1080
gttaccttca tcgccaagaa actctttaaa gacaagatca acattacta cgtcccggat    1140 ttcaagcttg ctatcgacca ttttgtatt catgccggag gcagagccgt gatcgatgtg    1200
ctacagaaga acttaggtct attgccgatc gatgtggagg catctaggtc aacgttacat    1260
agatttggga acacttcgtc tagctcaatt tggtatgaat tggcgtacat agaggcaaaa    1320
ggaaggatga agagagggaa caaagtttgg cagattgctt tagggtcagg gtttaagtgt    1380
aatagtgcgg tttgggtggc tctacgcaat gtcaaggctt cgacaaatag tccttgggaa    1440
cattgcattg atagatatcc agatgcaatt gattctgatt cgggtaagtc agagactcgt    1500
gtccaaaacg gtcggtccta a                                              1521
```

<210> SEQ ID NO 12
<211> LENGTH: 339
<212> TYPE: PRT
<213> ORGANISM: Artificial Sequence
<220> FEATURE:
<223> OTHER INFORMATION: modified Thlaspi arvense FAE1 sequence

<400> SEQUENCE: 12

```
Met Thr Ser Val Asn Val Lys Leu Leu Tyr His Tyr Val Ile Thr Asn
1               5                   10                  15

Phe Phe Asn Leu Cys Phe Phe Pro Leu Ala Ala Ile Val Ala Gly Lys
            20                  25                  30

Ala Ser Arg Leu Thr Thr Asn Asp Leu His His Phe Tyr Tyr Ser Tyr
        35                  40                  45

Leu Gln His Asn Leu Ile Thr Ile Ser Leu Leu Phe Ala Phe Thr Val
    50                  55                  60

Phe Gly Leu Ala Leu Tyr Ile Val Thr Arg Pro Lys Pro Val Tyr Leu
65                  70                  75                  80

Val Asp His Ser Cys Tyr Leu Pro Pro Ser His Leu Arg Ser Ser Ile
                85                  90                  95
```

Ser Lys Val Met Asp Ile Phe Tyr Gln Val Arg Leu Ala Asp Pro Leu
                100                 105                 110

Arg Asn Ala Ala Ser Asp Asp Ser Ser Trp Leu Asp Phe Leu Arg Lys
            115                 120                 125

Ile Gln Glu Arg Ser Gly Leu Gly Asp Glu Thr His Gly Pro Glu Gly
        130                 135                 140

Leu Leu Gln Val Pro Pro Arg Lys Thr Phe Ala Ala Arg Glu Glu
145                 150                 155                 160

Thr Glu Gln Val Ile Ile Gly Ala Leu Glu Lys Leu Phe Glu Asn Thr
                165                 170                 175

Lys Val Asn Pro Lys Glu Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Ile Arg Ser Phe Asn Leu Gly Gly Met Gly Cys Ser
    210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
            260                 265                 270

Arg Val Gly Gly Ala Ala Ile Leu Leu Ser Asn Lys Pro Arg Asp Arg
        275                 280                 285

Arg Arg Ser Lys Tyr Gln Leu Leu His Thr Val Arg Thr His Thr Gly
    290                 295                 300

Ala Asp Asp Lys Ser Phe Arg Cys Val Gln Gln Glu Asp Asp Glu Ser
305                 310                 315                 320

Gly Lys Thr Gly Val Cys Leu Ser Lys Asp Ile Thr Gly Val Ala Gly
                325                 330                 335

Arg Thr Val

<210> SEQ ID NO 13
<211> LENGTH: 1521
<212> TYPE: DNA
<213> ORGANISM: Artificial Sequence
<220> FEATURE:
<223> OTHER INFORMATION: modified Thlaspi arvense FAE1 sequence

<400> SEQUENCE: 13
atgacgtccg ttaacgttaa gctcctttac cattacgtca tcaccaactt tttcaacctt      60
tgcttcttcc cgttagcggc gatcgttgcc ggaaaagcct ctcggcttac cacaaacgat     120
cttcaccact tctactattc ctatctccaa cacaacctaa taccatatc tctactcttt     180 gccttcaccg tttcggttt ggctctctac atcgtaaccc ggcccaaacc ggtttacctc     240
gttgaccatt cctgctacct tccaccatcg catcttagaa gcagtatctc taaggtcatg     300
gatatcttct atcaagtaag attagccgat cctttacgga acgcggcaag cgatgattcg     360
tcctggcttg atttcttgag gaagattcag gagcggtctg gtctaggcga tgaaacccac     420
ggccccgagg gactgcttca ggtccctcca cggaagactt tgccgcggc gcgtgaagaa     480 acagagcaag tgatcatcgg tgcgctcgaa aaactattcg agaacaccaa agttaaccct     540
aaagagattg gtatacttgt ggtgaactca agcatgttta atccgactcc ttcgctctcg     600
gcgatggttg ttaatacttt caagctccga agcaacatca gaagctttaa tcttggagga     660

```
atgggttgta gtgccggcgt tatagccatt gatctggcta aggacttgtt gcatgtccat    720
aaaaacactt atgctcttgt ggtgagcaca gagaacatca cttacaacat ttatgctggt    780
gataacagat ccatgatggt ttcgaattgc ttgttccgtg ttggtggggc cgcgattttg    840
ctctccaaca agccgaggga ccggagacgg tccaagtacc agctacttca cacggttcgg    900
acgcataccg gagctgacga caagtctttc cgatgtgtgc aacaagaaga cgacgagagc    960
ggtaaaaccg gggtgtgttt gtccaaggac ataaccggtg ttgccgggag aactgttcag   1020
aaaaacataa caacattggg tccgttggtt cttccttta gcgagaaatt tcttttttc    1080 gttaccttca tcgccaagaa actctttaaa gacaagatca acattacta cgtcccggat   1140 ttcaagcttg ctatcgacca ttttgtatt catgccggag gcagagccgt gatcgatgtg   1200
ctacagaaga acttaggtct attgccgatc gatgtggagg catctaggtc aacgttacat   1260
agatttggga acacttcgtc tagctcaatt tggtatgaat tggcgtacat agaggcaaaa   1320
ggaaggatga agagagggaa caaagtttag cagattgctt tagggtcagg gtttaagtgt   1380
aatagtgcgg tttgggtggc tctacgcaat gtcaaggctt cgacaaatag tccttgggaa   1440
cattgcattg atagatatcc agatgcaatt gattctgatt cgggtaagtc agagactcgt   1500
gtccaaaacg gtcggtccta a                                             1521
```

<210> SEQ ID NO 14
<211> LENGTH: 449
<212> TYPE: PRT
<213> ORGANISM: Artificial Sequence
<220> FEATURE:
<223> OTHER INFORMATION: modified Thlaspi arvense FAE1 sequence

<400> SEQUENCE: 14

```
Met Thr Ser Val Asn Val Lys Leu Leu Tyr His Tyr Val Ile Thr Asn
1               5                   10                  15

Phe Phe Asn Leu Cys Phe Phe Pro Leu Ala Ala Ile Val Ala Gly Lys
            20                  25                  30

Ala Ser Arg Leu Thr Thr Asn Asp Leu His His Phe Tyr Tyr Ser Tyr
        35                  40                  45

Leu Gln His Asn Leu Ile Thr Ile Ser Leu Leu Phe Ala Phe Thr Val
    50                  55                  60

Phe Gly Leu Ala Leu Tyr Ile Val Thr Arg Pro Lys Pro Val Tyr Leu
65                  70                  75                  80

Val Asp His Ser Cys Tyr Leu Pro Pro Ser His Leu Arg Ser Ser Ile
                85                  90                  95

Ser Lys Val Met Asp Ile Phe Tyr Gln Val Arg Leu Ala Asp Pro Leu
            100                 105                 110

Arg Asn Ala Ala Ser Asp Asp Ser Ser Trp Leu Asp Phe Leu Arg Lys
        115                 120                 125

Ile Gln Glu Arg Ser Gly Leu Gly Asp Glu Thr His Gly Pro Glu Gly
    130                 135                 140

Leu Leu Gln Val Pro Pro Arg Lys Thr Phe Ala Ala Arg Glu Glu
145                 150                 155                 160

Thr Glu Gln Val Ile Ile Gly Ala Leu Glu Lys Leu Phe Glu Asn Thr
                165                 170                 175

Lys Val Asn Pro Lys Glu Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205
```

Leu Arg Ser Asn Ile Arg Ser Phe Asn Leu Gly Gly Met Gly Cys Ser
210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
                260                 265                 270

Arg Val Gly Gly Ala Ala Ile Leu Leu Ser Asn Lys Pro Arg Asp Arg
            275                 280                 285

Arg Arg Ser Lys Tyr Gln Leu Leu His Thr Val Arg Thr His Thr Gly
        290                 295                 300

Ala Asp Asp Lys Ser Phe Arg Cys Val Gln Gln Glu Asp Asp Glu Ser
305                 310                 315                 320

Gly Lys Thr Gly Val Cys Leu Ser Lys Asp Ile Thr Gly Val Ala Gly
                325                 330                 335

Arg Thr Val Gln Lys Asn Ile Thr Thr Leu Gly Pro Leu Val Leu Pro
                340                 345                 350

Phe Ser Glu Lys Phe Leu Phe Phe Val Thr Phe Ile Ala Lys Lys Leu
            355                 360                 365

Phe Lys Asp Lys Ile Lys His Tyr Tyr Val Pro Asp Phe Lys Leu Ala
        370                 375                 380

Ile Asp His Phe Cys Ile His Ala Gly Gly Arg Ala Val Ile Asp Val
385                 390                 395                 400

Leu Gln Lys Asn Leu Gly Leu Leu Pro Ile Asp Val Glu Ala Ser Arg
                405                 410                 415

Ser Thr Leu His Arg Phe Gly Asn Thr Ser Ser Ser Ile Trp Tyr
                420                 425                 430

Glu Leu Ala Tyr Ile Glu Ala Lys Gly Arg Met Lys Arg Gly Asn Lys
        435                 440                 445

Val

<210> SEQ ID NO 15
<211> LENGTH: 20
<212> TYPE: DNA
<213> ORGANISM: Artificial Sequence
<220> FEATURE:
<223> OTHER INFORMATION: guide sequence that can be used to direct a Cas
      nuclease to the FAE1 gene

<400> SEQUENCE: 15
tggctctcta catcgtaacc                                                   20

<210> SEQ ID NO 16
<211> LENGTH: 24
<212> TYPE: DNA
<213> ORGANISM: Artificial Sequence
<220> FEATURE:
<223> OTHER INFORMATION: synthetic primer

<400> SEQUENCE: 16
attgtggctc tctacatcgt aacc                                              24

<210> SEQ ID NO 17
<211> LENGTH: 24
<212> TYPE: DNA
<213> ORGANISM: Artificial Sequence
<220> FEATURE:
<223> OTHER INFORMATION: synthetic primer

```
<400> SEQUENCE: 17
aaacggttac gatgtagaga gcca                                          24

<210> SEQ ID NO 18
<211> LENGTH: 22
<212> TYPE: DNA
<213> ORGANISM: Artificial Sequence
<220> FEATURE:
<223> OTHER INFORMATION: synthetic primer

<400> SEQUENCE: 18
acatgcatgt aaaacgtaac gg                                            22

<210> SEQ ID NO 19
<211> LENGTH: 22
<212> TYPE: DNA
<213> ORGANISM: Artificial Sequence
<220> FEATURE:
<223> OTHER INFORMATION: synthetic primer

<400> SEQUENCE: 19
tggattatat caggatgtgg cg                                            22
```

PLANTS HAVING INCREASED OIL QUALITY

CROSS-REFERENCE TO RELATED APPLICATIONS

This application claims the benefit of U.S. Patent Application Ser. No. 62/451,467, filed on Jan. 27, 2017. The disclosure of the prior application is considered part of (and is incorporated by reference in) the disclosure of this application.

STATEMENT REGARDING FEDERAL FUNDING

This invention was made with government support under 2014-67009-22305 awarded by the United States Department of Agriculture. The government has certain rights in the invention.

BACKGROUND

1. Technical Field

This document relates to materials and methods for generating oilseed (e.g., pennycress) plants that have low levels of erucic acid. For example, this document provides oilseed plants having reduced expression levels of one or more polypeptides involved in erucic acid metabolism (e.g., fatty acid elongase 1 (FAE1)), as well as materials and methods for making and using oilseed plants having low levels of erucic acid.

2. Background Information

Oilseed crops are sources of oils and seed meal having a multitude of uses. Winter annual varieties of pennycress (*Thlaspi arvense* L.) have been developed into a new crop species that can be grown on the fallow land available between the harvest of corn and the sowing of soybeans the following year (Phippen et al., 2012 *Crop Science*, 52:2767-2773). There are over eighty million acres undergoing the corn/soybean rotation that could be used for double cropping pennycress. Pennycress can yield over 2000 pounds per acre of oilseeds that naturally contain up to 35% oil (Boateng et al., 2010 *Energy & Fuels*, 24:6624-6632; and Warwick et al., 2002 *Canadian Journal of Plant Science*, 82:803-823) with erucic acid making up the largest fraction (31%-39%) of the fatty acids in the natural oil (Moser et al., 2009 *Industrial Crops and Products*, 30:199-205). The extracted oil can be easily converted into a variety of biofuels including biodiesel and jet fuel (Moser et al., 2009 *Energy & Fuels*, 23:4149-4155). However, natural levels of erucic acid in wild pennycress strains make pennycress oil inedible for human consumption (Bell, 1993 *Canadian Journal of Animal Science*, 73:679-697), and render pennycress oil of suboptimal quality for both biofuel and food production.

SUMMARY

This document provides materials and methods for generating oilseed crops (e.g., pennycress) with low levels of erucic acid. For example, this document provides pennycress plants having reduced expression levels of one or more polypeptides involved in erucic acid metabolism (e.g., FAE1), as compared to corresponding wild type pennycress plants, as well as materials and methods for making and using pennycress plants having low levels of erucic acid. High erucic acid levels in seed oil can lead to the contamination and toxicity of canola oil. For example, the ingestion of oils containing high levels of erucic acid has been associated with myocardial lipidosis. Since 1956 the FDA has considered such oils as unfit for human consumption. Internationally accepted erucic acid level thresholds for canola are that it must be below 2%.

As demonstrated herein, loss-of-function modifications in the pennycress FAE1 gene (e.g., a four base-pair deletion, a single base-pair insertion, a single base-pair deletion, or a single base-pair substitution) resulted in low levels of erucic acid (22:1) and eicosenoic acid (20:1), and increased levels of oleic acid (18:1), linoleic acid (18:2), and linolenic acid (18:3), as compared to corresponding wild type pennycress plants. The oil from this low level erucic acid pennycress contains less than 2% erucic acid, thus making the pennycress fit for human consumption. In addition, the pennycress is likely to be more suitable as an animal feed supplement, especially for monogastric livestock, as it has increased levels of linoleic and linolenic acids that may render it useful for specialized feed, bioproduct formation, and provide enhanced nutritional value.

In general, one aspect of this document features an oilseed plant having low levels of erucic acid as compared to a corresponding wild type oilseed plant. The oilseed plant can be a pennycress plant. The low levels of erucic acid can include less than about 5% erucic acid (e.g., less than about 2% erucic acid). The oilseed plant can include a modification in the coding sequence of a gene encoding a polypeptide involved in erucic acid biosynthesis. The gene encoding a polypeptide involved in erucic acid biosynthesis can be an FAE1 gene. The modification can be a loss-of-function modification. The modified FAE1 coding sequence can include a deletion. The deletion can be a 4 base-pair deletion. An example of an FAE1 coding sequence with a 4 base-pair deletion is set forth in SEQ ID NO:3. The modified FAE1 coding sequence can encode a truncated and/or degraded FAE1 polypeptide. An example of a truncated FAE1 polypeptide encoded by an FAE1 coding sequence with a 4 base-pair deletion is set forth in SEQ ID NO:4. The modified FAE1 coding sequence can include an insertion. The insertion can be a single base-pair insertion (e.g., an adenine ('A') insertion). An example of an FAE1 coding sequence with an 'A' insertion is set forth in SEQ ID NO:5. The modified FAE1 coding sequence can encode a truncated and/or degraded FAE1 polypeptide. An example of a truncated FAE1 polypeptide encoded by an FAE1 coding sequence with an 'A' insertion is set forth in SEQ ID NO:6. The oilseed plant also can include low levels of eicosenoic acid as compared to a corresponding wild type oilseed plant. The low levels of eicosenoic acid can include less than 2% eicosenoic acid. The oilseed plant also can include increased levels of oleic acid as compared to a corresponding wild type oilseed plant. The increased levels of oleic acid can include about 25% to about 55% oleic acid. The oilseed plant also can include increased levels of linoleic acid as compared to a corresponding wild type oilseed plant. The increased levels of linoleic acid can include about 20% to about 40% linoleic acid. The oilseed also can include increased levels of linolenic acid as compared to a corresponding wild type oilseed plant. The increased levels of linolenic acid can include about 13% to about 30% linolenic acid. This document also features a seed produced by an oilseed plant having low levels of erucic acid as compared to a corresponding wild type oilseed plant.

In another aspect, this document features a method for generating an oilseed plant having low levels of erucic acid as compared to a corresponding wild type oilseed plant. The method can include, or consist essentially of, modifying the coding sequence of a gene in the oilseed plant genome, where the gene encodes a polypeptide involved in erucic acid biosynthesis, and where the modification is effective to reduce erucic acid biosynthesis in the plant. The oilseed plant can be a pennycress plant. The modifying step can include site-specific editing or mutagenesis. The low levels of erucic acid can include less than about 2% erucic acid. The gene encoding a polypeptide involved in erucic acid biosynthesis can be an FAE1 gene. The modified FAE1 coding sequence can include a deletion. The deletion can be a 4 base-pair deletion. An example of a modified FAE1 coding sequence having a 4 base-pair deletion is set forth in SEQ ID NO:3. The modified FAE1 coding sequence can encode a truncated FAE1 polypeptide. An example of a truncated and/or degraded FAE1 polypeptide encoded by an FAE1 coding sequence with a 4 base-pair deletion is set forth in SEQ ID NO:4. The modified FAE1 coding sequence can include an insertion. The insertion can be a single base-pair insertion (e.g., an adenine ('A') insertion). An example of an FAE1 coding sequence with an 'A' insertion is set forth in SEQ ID NO:5. The modified FAE1 coding sequence can encode a truncated and/or degraded FAE1 polypeptide. An example of a truncated FAE1 polypeptide encoded by an FAE1 coding sequence with an 'A' insertion is set forth in SEQ ID NO:6.

Another aspect of this document features an oilseed plant having low levels of erucic acid as compared to a corresponding wild type oilseed plant, where the oilseed plant includes a genome edited in a site-specific manner to modify the coding sequence of the FAE1 gene, where the modified FAE1 coding sequence is effective to cause low levels of erucic acid as compared to a wild type oilseed plant. The oilseed plant can be a pennycress plant. The low levels of erucic acid can include less than about 5% erucic acid (e.g., less than about 2% erucic acid). The modification can be a loss-of-function modification. The modified FAE1 coding sequence can include a deletion. The deletion can be a 4 base-pair deletion. An example of an FAE1 coding sequence with a 4 base-pair deletion is set forth in SEQ ID NO:3. The modified FAE1 coding sequence can encode a truncated and/or degraded FAE1 polypeptide. An example of a truncated FAE1 polypeptide encoded by an FAE1 coding sequence with a 4 base-pair deletion is set forth in SEQ ID NO:4. The modified FAE1 coding sequence can include an insertion. The insertion can be a single base-pair insertion (e.g., an adenine ('A') insertion). An example of an FAE1 coding sequence with an 'A' insertion is set forth in SEQ ID NO:5. The modified FAE1 coding sequence can encode a truncated and/or degraded FAE1 polypeptide. An example of a truncated FAE1 polypeptide encoded by an FAE1 coding sequence with an 'A' insertion is set forth in SEQ ID NO:6. The oilseed plant also can include low levels of eicosenoic acid as compared to a corresponding wild type oilseed plant. The low levels of eicosenoic acid can include less than 2% eicosenoic acid. The oilseed plant also can include increased levels of oleic acid as compared to a corresponding wild type oilseed plant. The oilse increased levels of oleic acid can include about 25% to about 55% oleic acid. The oilseed plant also can include increased levels of linoleic acid as compared to a corresponding wild type oilseed plant. The increased levels of linoleic acid can include about 20% to about 40% linoleic acid. The oilseed plant also can include increased levels of linolenic acid as compared to a corresponding wild type oilseed plant. The increased levels of linolenic acid comprise about 13% to about 30% linolenic acid. This document also features a seed produced by an oilseed plant having low levels of erucic acid as compared to a corresponding wild type oilseed plant, where the oilseed plant includes a genome edited in a site-specific manner to modify the coding sequence of the FAE1 gene, where the modified FAE1 coding sequence is effective to cause low levels of erucic acid as compared to a wild type oilseed plant.

In another aspect, this document features a method for generating an oilseed plant having low levels of erucic acid as compared to a corresponding wild type oilseed plant. The method can include, or consist essentially of, introducing into an oilseed plant cell a nuclease and a guide sequence, where the guide sequence includes a nucleic acid sequence specific to the FAE1 gene; selecting an oilseed plant cell having low levels of erucic acid as compared to a wild oilseed plant; and regenerating an oilseed plant having low levels of erucic acid from the selected oilseed plant cell. The oilseed plant can be a pennycress plant. The nuclease can be a CRISPR associated (Cas) nuclease. The Cas nuclease can be a Cas9 nuclease (e.g., a *Streptococcus pyogenes* Cas9). The guide sequence can include SEQ ID NO:15. The FAE1 gene can include a modified FAE1 coding sequence. The modified FAE1 coding sequence can include a deletion. The deletion can be a 4 base-pair deletion. An example of an FAE1 coding sequence with a 4 base-pair deletion is set forth in SEQ ID NO:3. The modified FAE1 coding sequence can encode a truncated and/or degraded FAE1 polypeptide. An example of a truncated FAE1 polypeptide encoded by an FAE1 coding sequence with a 4 base-pair deletion is set forth in SEQ ID NO:4. The modified FAE1 coding sequence can include an insertion. The insertion can be a single base-pair insertion (e.g., an adenine ('A') insertion). An example of an FAE1 coding sequence with an 'A' insertion is set forth in SEQ ID NO:5. The modified FAE1 coding sequence can encode a truncated and/or degraded FAE1 polypeptide. An example of a truncated FAE1 polypeptide encoded by an FAE1 coding sequence with an 'A' insertion is set forth in SEQ ID NO:6. The low levels of erucic acid can include less than about 2% erucic acid.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 8A is a photograph of plant morphology of a WT, a control, a −4 bp fae1 homozygous mutant plant, and a +A fae1 homozygous mutant plant. FIG. 8B is a graph showing the average heights of WT, control, −4 bp fae1 homozygous mutant, and +A fae1 homozygous mutant plants. FIG. 8C is a graph showing the total average seed weights of WT, control, −4 bp fae1 homozygous mutant plant, and +A fae1 homozygous mutant plants.

DETAILED DESCRIPTION

Figure 1:
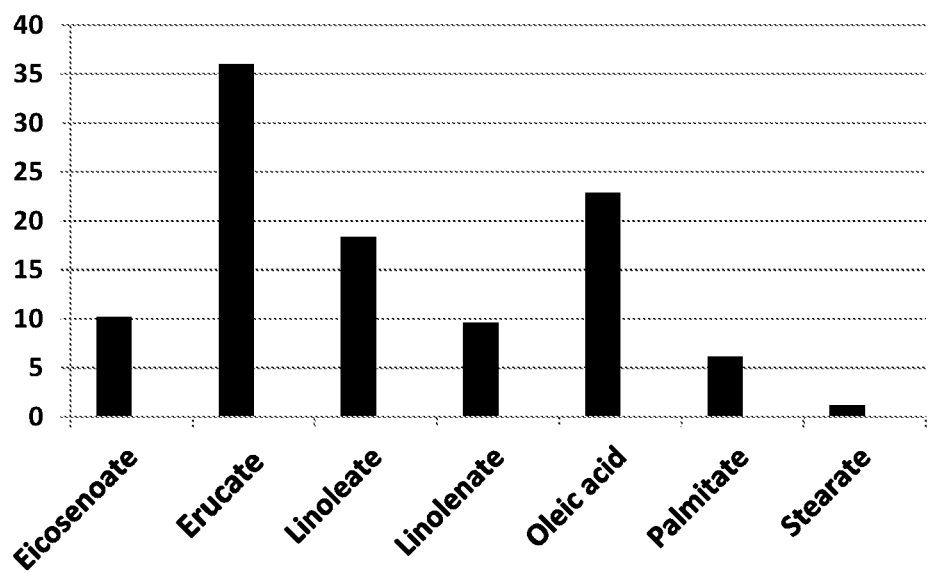
FIG. 1 is a graph of the fatty acid composition of pennycress seed oil.
Figure 2:
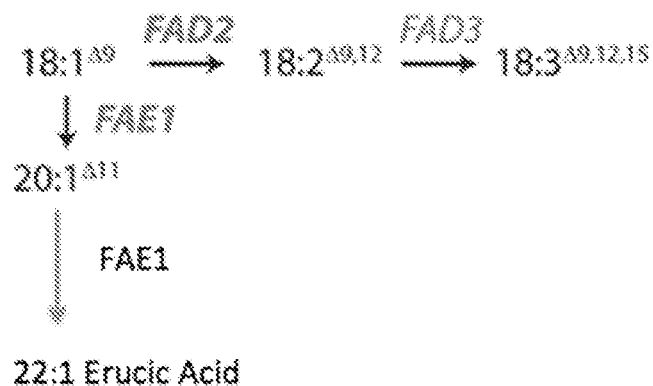
FIG. 2 is a schematic showing a fatty acid biosynthesis pathway starting with oleic acid. Erucic acid is composed of 22 carbons and contains one double bond (referred to as 22:1). Erucic acid is derived from oleic acid (18:1) by the addition of two carbons to produce eicosenoic acid (20:1) and then two additional carbons to produce erucic acid (22:1). Two additional fatty acids linoleic acid (18:2) and linolenic acid (18:3) are also derived from oleic acid.

This document relates to oilseed (e.g., pennycress) plants that have low levels of erucic acid. In some cases, this document provides oilseed plants having reduced expression levels of one or more polypeptides involved in erucic acid biosynthesis (e.g., FAE1) as compared to corresponding wild type pennycress plants. For example, an oilseed plant having low levels of erucic acid can have one or more modifications in an FAE1 gene effective to reduce FAE1 polypeptide expression and/or reduce FAE1 polypeptide function. This document also relates to methods and materials for making and using oilseed plants having low levels of erucic acid. In some cases, site-specific gene editing can be used to modify an FAE1 gene. For example, site-specific editing can be used to modify the FAE1 gene in an oilseed plant genome to reduce FAE1 polypeptide expression and/or reduce FAE1 polypeptide function. As described herein, gene editing techniques (e.g., CRISPR/Cas systems) can be used to produce an oilseed plant having a loss-of-function modification in an FAE1 gene. For example, one or more modifications can be made to an FAE1 gene in a plant, which can be effective to cause reduced expression of an FAE1 polypeptide and thereby reduce erucic acid biosynthesis in the plant.

The oilseed plants having low levels of erucic acid as described herein can be derived from any appropriate species of oilseed plant. An oilseed plant can be a monocotyledonous oilseed plant. An oilseed plant can be a dicotyledonous oilseed plant. An oilseed plant can be a member of the family Brassicaceae (e.g., the mustard family). For example, an oilseed plant can be a member of the genus Brassica. Examples of oilseed plants include, without limitation, pennycress, rapeseed, soybean, sunflower, canola, flax, camelina, carinata, crambe, and lepidium plants. In some cases, an oilseed plant having low levels of erucic acid as described herein can be a pennycress plant.

The oilseed plants having low levels of erucic acid as described herein can have low levels of erucic acid in one or more plant tissues. In some cases, an oilseed plant having low levels of erucic acid as described herein can have low levels of erucic acid in the seeds. In other cases, an oilseed plant (or any plant) can have low levels of erucic acid in vegetative and storage tissues (e.g., natural and/or man-made) including stems, leaves, roots, and tubers.

The term "low level" as used herein with respect to a level of erucic acid in the oil obtained from an oilseed plant refers to any level that is lower than a reference level of erucic acid. The term "reference level" as used herein with respect to erucic acid refers to the level of erucic acid typically observed in the oil obtained from a wild type oilseed plant. It will be appreciated that levels of erucic acid in the oil obtained from a from comparable oilseed plants are used when determining whether or not the level of erucic acid in the oil obtained from a particular oilseed plant is a low level. For example, a wild type pennycress plant typically produces oil having about 30% to about 39% (by weight) erucic acid (Sedbrook et al., 2014 *Plant Science* 227:122-132). In some cases, a pennycress plant having low levels of erucic acid as described herein can produce oil having about 0% to about 30% (by weight) erucic acid. In some cases, a low level of erucic acid can be a level that is less than about 25% (by weight) erucic acid (e.g., less than about 20%, less than about 15%, less than about 10%, less than about 5%, less than about 4%, less than about 3%, less than about 2%, less than about 1%, or less than about 0.5% (by weight) erucic acid). For example, the oilseed plants having low levels of erucic acid described herein can produce oil having less than 2% (by weight) erucic acid.

The oilseed plants having low levels of erucic acid described herein also can have low levels of eicosenoic acid (20:1). In some cases, a low level of eicosenoic acid can be a level that is less than about 10% (by weight) eicosenoic acid (e.g., less than about 8%, less than about 6%, less than about 5%, less than about 4%, less than about 3%, less than about 2%, less than about 1%, or less than about 0.5% (by weight) eicosenoic acid). For example, the oilseed plants having low levels of eicosenoic acid described herein can have less than 2% (by weight) eicosenoic acid.

The oilseed plants having low levels of erucic acid described herein also can have increased levels of oleic acid (18:1), linoleic acid (18:2), and/or linolenic acid (18:3). In some cases, an increased level of oleic acid, linoleic acid and/or linolenic acid can be a level that is about 30% greater than a reference level of oleic acid, linoleic acid, and/or linolenic acid (e.g., the level typically observed in a wild type oilseed plant). For example, a pennycress plant having in an increased level of oleic acid can have about 25% to about 55% (by weight) oleic acid (e.g., about 45% to about 50% (by weight) oleic acid), a pennycress plant having in an increased level of linoleic acid can have about 20% to about 40% (by weight) linoleic acid (e.g., about 25% to about 30% (by weight) linoleic acid), and a pennycress plant having in an increased level of linolenic acid can have about 13% to about 30% (by weight) linolenic acid (e.g., about 15% to about 20% (by weight) linolenic acid).

The oilseed plants having low levels of erucic acid as described herein can be from the V296, V297, or V300 line as described, for example, in Example 1, or can be progeny derived from those lines.

The oilseed plants having low levels of erucic acid as described herein can include one or more modifications in a gene that encodes a polypeptide involved in erucic acid biosynthesis. In some cases, the one or more modification in a gene that encodes a polypeptide involved in erucic acid biosynthesis can be in the coding sequence. Polypeptides involved in erucic acid biosynthesis include, without limitation, fatty acid elongases (e.g., FAE1) and polypeptides involved in the regulation of fatty acid elongases (e.g., of expression, activity, and/or degradation). A representative WT pennycress FAE1 coding sequence is as follows (SEQ ID NO: 1):

ATGACGTCCGTTAACGTTAAGCTCCTTTACCATTACGTCATCACCAACTT

TTTCAACCTTTGCTTCTTCCCGTTAGCGGCGATCGTTGCCGGAAAAGCCT

CTCGGCTTACCACAAACGATCTTCACCACTTCTACTATTCCTATCTCCAA

CACAACCTAATAACCATATCTCTACTCTTTGCCTTCACCGTTTTCGGTTT

GGCTCTCTACATCGTAACCCGGCCCAAACCGGTTTACCTCGTTGACCATT

CCTGCTACCTTCCACCATCGCATCTTAGAAGCAGTATCTCTAAGGTCATG

GATATCTTCTATCAAGTAAGATTAGCCGATCCTTTACGGAACGCGGCAAG

CGATGATTCGTCCTGGCTTGATTTCTTGAGGAAGATTCAGGAGCGGTCTG

GTCTAGGCGATGAAACCCACGGCCCCGAGGGACTGCTTCAGGTCCCTCCA

CGGAAGACTTTTGCCGCGGCGCGTGAAGAAACAGAGCAAGTGATCATCGG

TGCGCTCGAAAAACTATTCGAGAACACCAAAGTTAACCCTAAAGAGATTG

GTATACTTGTGGTGAACTCAAGCATGTTTAATCCGACTCCTTCGCTCTCG

GCGATGGTTGTTAATACTTTCAAGCTCCGAAGCAACATCAGAAGCTTTAA

TCTTGGAGGAATGGGTTGTAGTGCCGGCGTTATAGCCATTGATCTGGCTA

AGGACTTGTTGCATGTCCATAAAAACACTTATGCTCTTGTGGTGAGCACA

GAGAACATCACTTACAACATTTATGCTGGTGATAACAGATCCATGATGGT

TTCGAATTGCTTGTTCCGTGTTGGTGGGGCCGCGATTTTGCTCTCCAACA

AGCCGAGGGACCGGAGACGGTCCAAGTACCAGCTACTTCACACGGTTCGG

ACGCATACCGGAGCTGACGACAAGTCTTTCCGATGTGTGCAACAAGAAGA

CGACGAGAGCGGTAAAACCGGGGTGTGTTTGTCCAAGGACATAACCGGTG

TTGCCGGGAGAACTGTTCAGAAAAACATAACAACATTGGGTCCGTTGGTT

CTTCCTTTTAGCGAGAAATTTCTTTTTTTCGTTACCTTCATCGCCAAGAA

ACTCTTTAAAGACAAGATCAAACATTACTACGTCCCGGATTTCAAGCTTG

CTATCGACCATTTTTGTATTCATGCCGGAGGCAGAGCCGTGATCGATGTG

CTACAGAAGAACTTAGGTCTATTGCCGATCGATGTGGAGGCATCTAGGTC

AACGTTACATAGATTTGGGAACACTTCGTCTAGCTCAATTTGGTATGAAT

TGGCGTACATAGAGGCAAAAGGAAGGATGAAGAGAGGGAACAAAGTTTGG

CAGATTGCTTTAGGGTCAGGGTTTAAGTGTAATAGTGCGGTTTGGGTGGC

TCTACGCAATGTCAAGGCTTCGACAAATAGTCCTTGGGAACATTGCATTG

ATAGATATCCAGATGCAATTGATTCTGATTCGGGTAAGTCAGAGACTCGT

GTCCAAAACGGTCGGTCCTAA

In some cases, a WT pennycress FAE1 gene can have a sequence that deviates from the sequence set forth above (SEQ ID NO:1), sometimes referred to as a variant sequence, provided the variant sequence encodes a WT pennycress FAE1 polypeptide. A representative WT pennycress FAE1 polypeptide is as follows (SEQ ID NO:2):

MTSVNVKLLYHYVITNFFNLCFFPLAAIVAGKASRLTTNDLHHFYYSYLQ

HNLITISLLFAFTVFGLALYIVTRPKPVYLVDHSCYLPPSHLRSSISKVM

DIFYQVRLADPLRNAASDDSSWLDFLRKIQERSGLGDETHGPEGLLQVPP

RKTFAAAREETEQVIIGALEKLFENTKVNPKEIGILVVNSSMFNPTPSLS

AMVVNTFKLRSNIRSFNLGGMGCSAGVIAIDLAKDLLHVHKNTYALVVST

ENITYNIYAGDNRSMMVSNCLFRVGGAAILLSNKPRDRRRSKYQLLHTVR

THTGADDKSFRCVQQEDDESGKTGVCLSKDITGVAGRTVQKNITTLGPLV

LPFSEKFLFFVTFIAKKLFKDKIKHYYVPDFKLAIDHFCIHAGGRAVIDV

LQKNLGLLPIDVEASRSTLHRFGNTSSSSIWYELAYIEAKGRMKRGNKVW

QIALGSGFKCNSAVWVALRNVKASTNSPWEHCIDRYPDAIDSDSGKSETR

VQNGRS

In some cases, a WT pennycress FAE1 polypeptide can have a sequence that deviates from the polypeptide sequence set forth above (SEQ ID NO:2), sometimes referred to as a variant sequence, provided the polypeptide maintains its WT function. For example, a FAE1 polypeptide can have at least 80 (e.g., at least 85, at least 90, at least 95, at least 98, or at least 99) percent sequence identity to SEQ ID NO:2. A FAE1 polypeptide can have one or more (e.g., 2, 3, 4, 5, 6, 7, 8, 9, or 10) amino acid modifications (e.g., substitutions) relative to SEQ ID NO:2.

In some cases, oilseed plants having low levels of erucic acid can include a loss-of-function modification in an FAE1 gene (e.g., in an FAE1 coding sequence). As used herein, a loss-of-function modification in an FAE1 gene can be any modification that is effective to reduce FAE1 polypeptide expression or FAE1 polypeptide function. In some cases, reduced FAE1 polypeptide expression or reduced FAE1 polypeptide function can be eliminated FAE1 polypeptide expression or eliminated FAE1 polypeptide function. Examples of genetic modifications include, without limitation, deletions, insertions, substitutions, frameshifts, duplications, and rearrangements. In some cases, a loss-of-function modification in an FAE1 coding sequence can result in a premature STOP codon. For example, a loss-of-function modification in an FAE1 coding sequence resulting in a premature STOP codon can produce a truncated and/or degraded (e.g., non-functional) polypeptide.

In some cases, oilseed plants having low levels of erucic acid described herein can include a deletion (e.g., a 4 base-pair deletion) relative to the WT pennycress FAE1 coding sequence (e.g., SEQ ID NO:1). For example, a modified FAE1 coding sequence can include a 4 base-pair deletion can be located adjacent to a PAM sequence in a WT pennycress FAE1 coding sequence (see, e.g., FIG. 7). A representative modified pennycress FAE1 coding sequence having a loss-of-function 4 base-pair deletion is as follows (SEQ ID NO:3):

ATGACGTCCGTTAACGTTAAGCTCCTTTACCATTACGTCATCACCAACTT

TTTCAACCTTTGCTTCTTCCCGTTAGCGGCGATCGTTGCCGGAAAAGCCT

CTCGGCTTACCACAAACGATCTTCACCACTTCTACTATTCCTATCTCCAA

CACAACCTAATAACCATATCTCTACTCTTTGCCTTCACCGTTTTCGGTTT

GGCTCTCTACATACCCGGCCCAAACCGGTTTACCTCGTTGACCATTCCTG

CTACCTTCCACCATCGCATCTTAGAAGCAGTATCTCTAAGGTCATGGATA

TCTTCTATCAAGTAAGATTAGCCGATCCTTTACGGAACGCGGCAAGCGAT

GATTCGTCCTGGCTTGATTTCTTGAGGAAGATTCAGGAGCGGTCTGGTCT

AGGCGATGAAACCCACGGCCCCGAGGGACTGCTTCAGGTCCCTCCACGGA

AGACTTTTGCCGCGGCGCGTGAAGAAACAGAGCAAGTGATCATCGGTGCG

CTCGAAAAACTATTCGAGAACACCAAAGTTAACCCTAAAGAGATTGGTAT

ACTTGTGGTGAACTCAAGCATGTTTAATCCGACTCCTTCGCTCTCGGCGA

TGGTTGTTAATACTTTCAAGCTCCGAAGCAACATCAGAAGCTTTAATCTT

GGAGGAATGGGTTGTAGTGCCGGCGTTATAGCCATTGATCTGGCTAAGGA

CTTGTTGCATGTCCATAAAAACACTTATGCTCTTGTGGTGAGCACAGAGA

ACATCACTTACAACATTTATGCTGGTGATAACAGATCCATGATGGTTTCG

AATTGCTTGTTCCGTGTTGGTGGGGCCGCGATTTTGCTCTCCAACAAGCC

GAGGGACCGGAGACGGTCCAAGTACCAGCTACTTCACACGGTTCGGACGC

ATACCGGAGCTGACGACAAGTCTTTCCGATGTGTGCAACAAGAAGACGAC

GAGAGCGGTAAAACCGGGGTGTGTTTGTCCAAGGACATAACCGGTGTTGC

CGGGAGAACTGTTCAGAAAAACATAACAACATTGGGTCCGTTGGTTCTTC

CTTTTAGCGAGAAATTTCTTTTTTTCGTTACCTTCATCGCCAAGAAACTC

TTTAAAGACAAGATCAAACATTACTACGTCCCGGATTTCAAGCTTGCTAT

CGACCATTTTTGTATTCATGCCGGAGGCAGAGCCGTGATCGATGTGCTAC

AGAAGAACTTAGGTCTATTGCCGATCGATGTGGAGGCATCTAGGTCAACG

TTACATAGATTTGGGAACACTTCGTCTAGCTCAATTTGGTATGAATTGGC

GTACATAGAGGCAAAAGGAAGGATGAAGAGAGGGAACAAAGTTTGGCAGA

TTGCTTTAGGGTCAGGGTTTAAGTGTAATAGTGCGGTTTGGGTGGCTCTA

CGCAATGTCAAGGCTTCGACAAATAGTCCTTGGGAACATTGCATTGATAG

ATATCCAGATGCAATTGATTCTGATTCGGGTAAGTCAGAGACTCGTGTCC

AAAACGGTCGGTCCTAA

A modified pennycress FAE1 coding sequence having a loss-of-function 4 base-pair deletion (e.g., SEQ ID NO:3) can result in a premature STOP codon and disruption of the gene. For example, a modified pennycress FAE1 coding sequence having a loss-of-function 4 base-pair deletion (e.g., SEQ ID NO:3) can encode a truncated FAE1 polypeptide. A representative truncated pennycress FAE1 polypeptide is as follows (SEQ ID NO:4):

MTSVNVKLLYHYVITNFFNLCFFPLAAIVAGKASRLTTNDLHHFYYSYLQ

HNLITISLLFAFTVFGLALYIPGPNRFTSLTIPATFHHRILEAVSLRSWI

SSIK

In some cases, oilseed plants having low levels of erucic acid described herein can include an insertion (e.g., a single base-pair insertion) relative to the WT pennycress FAE1 coding sequence (e.g., SEQ ID NO:1). The single base-pair insertion can be an insertion of any appropriate nucleotide. For example, a modified FAE1 coding sequence can include a single 'A' can be inserted five base-pairs upstream from the PAM in a WT pennycress FAE1 coding sequence (see, e.g., FIG. 7). A representative modified pennycress FAE1 coding sequence having a loss-of-function single 'A' base-pair insertion is as follows (SEQ ID NO:5):

ATGACGTCCGTTAACGTTAAGCTCCTTTACCATTACGTCATCACCAACTT

TTTCAACCTTTGCTTCTTCCCGTTAGCGGCGATCGTTGCCGGAAAAGCCT

CTCGGCTTACCACAAACGATCTTCACCACTTCTACTATTCCTATCTCCAA

CACAACCTAATAACCATATCTCTACTCTTTGCCTTCACCGTTTTCGGTTT

GGCTCTCTACATCGTAAACCCGGCCCAAACCGGTTTACCTCGTTGACCAT

TCCTGCTACCTTCCACCATCGCATCTTAGAAGCAGTATCTCTAAGGTCAT

GGATATCTTCTATCAAGTAAGATTAGCCGATCCTTTACGGAACGCGGCAA

GCGATGATTCGTCCTGGCTTGATTTCTTGAGGAAGATTCAGGAGCGGTCT

GGTCTAGGCGATGAAACCCACGGCCCCGAGGGACTGCTTCAGGTCCCTCC

ACGGAAGACTTTTGCCGCGGCGCGTGAAGAAACAGAGCAAGTGATCATCG

GTGCGCTCGAAAAACTATTCGAGAACACCAAAGTTAACCCTAAAGAGATT

GGTATACTTGTGGTGAACTCAAGCATGTTTAATCCGACTCCTTCGCTCTC

GGCGATGGTTGTTAATACTTTCAAGCTCCGAAGCAACATCAGAAGCTTTA

ATCTTGGAGGAATGGGTTGTAGTGCCGGCGTTATAGCCATTGATCTGGCT

AAGGACTTGTTGCATGTCCATAAAAACACTTATGCTCTTGTGGTGAGCAC

AGAGAACATCACTTACAACATTTATGCTGGTGATAACAGATCCATGATGG

TTTCGAATTGCTTGTTCCGTGTTGGTGGGGCCGCGATTTTGCTCTCCAAC

AAGCCGAGGGACCGGAGACGGTCCAAGTACCAGCTACTTCACACGGTTCG

```
GACGCATACCGGAGCTGACGACAAGTCTTTCCGATGTGTGCAACAAGAAG

ACGACGAGAGCGGTAAAACCGGGGTGTGTTTGTCCAAGGACATAACCGGT

GTTGCCGGGAGAACTGTTCAGAAAAACATAACAACATTGGGTCCGTTGGT

TCTTCCTTTTAGCGAGAAATTTCTTTTTTTCGTTACCTTCATCGCCAAGA

AACTCTTTAAAGACAAGATCAAACATTACTACGTCCCGGATTTCAAGCTT

GCTATCGACCATTTTTGTATTCATGCCGGAGGCAGAGCCGTGATCGATGT

GCTACAGAAGAACTTAGGTCTATTGCCGATCGATGTGGAGGCATCTAGGT

CAACGTTACATAGATTTGGGAACACTTCGTCTAGCTCAATTTGGTATGAA

TTGGCGTACATAGAGGCAAAAGGAAGGATGAAGAGAGGGAACAAAGTTTG

GCAGATTGCTTTAGGGTCAGGGTTTAAGTGTAATAGTGCGGTTTGGGTGG

CTCTACGCAATGTCAAGGCTTCGACAAATAGTCCTTGGGAACATTGCATT

GATAGATATCCAGATGCAATTGATTCTGATTCGGGTAAGTCAGAGACTCG

TGTCCAAAACGGTCGGTCCTAA
```

A modified pennycress FAE1 coding sequence having a loss-of-function single 'A' base-pair insertion (e.g., SEQ ID NO:5) can result in a premature STOP codon and disruption of the gene. For example, a modified pennycress FAE1 coding sequence having a loss-of-function single 'A' base-pair insertion (e.g., SEQ ID NO:5) can encode a truncated FAE1 polypeptide. A representative truncated pennycress FAE1 polypeptide is as follows (SEQ ID NO:6):

```
MTSVNVKLLYHYVITNFFNLCFFPLAAIVAGKASRLTTNDLHHFYYSYLQ

HNLITISLLFAFTVFGLALYIVNPAQTGLPR
```

Figure 7:
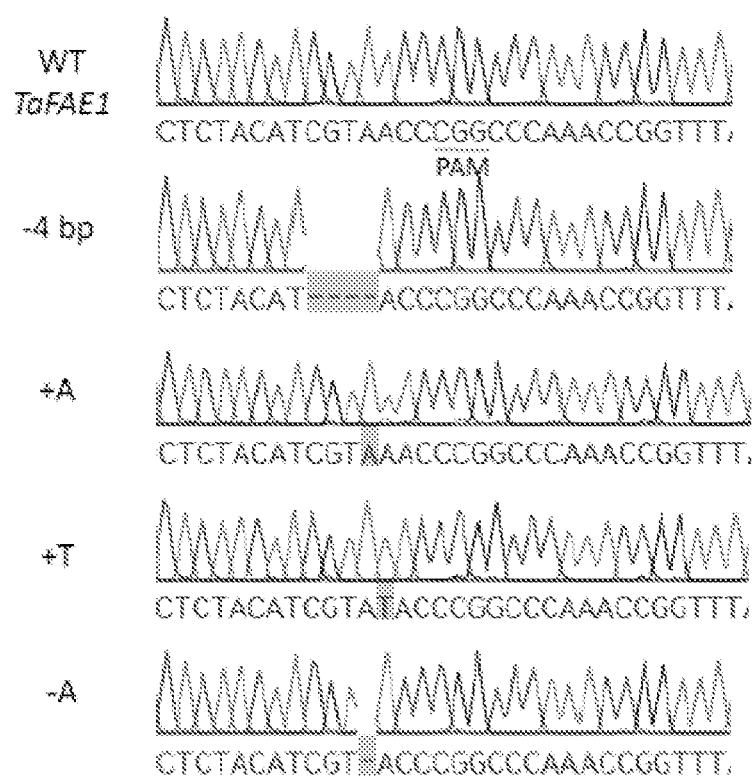
FIG. 7 contains sequencing reads showing the wild type (WT) pennycress FAE1 sequence (residues 205 to 235 of SEQ ID NO:1), and four FAE1 loss-of-function mutations: a 4 base-pair deletion (−4 bp) sequence four base-pairs upstream from the CRISPR/Cas9 protospacer adjacent motif (PAM) site (residues 205 to 231 of SEQ ID NO:3), a single base-pair insertion of an 'A' (+A) five base-pairs upstream from the CRISPR/Cas9 PAM site (residues 205 to 236 of SEQ ID NO:5), a single base-pair insertion of a 'T' (+T) four base-pairs upstream from the CRISPR/Cas9 PAM site (residues 205 to 236 of SEQ ID NO:7), and a single base-pair deletion (−A bp) sequence four base-pairs upstream from the CRISPR/Cas9 PAM site (residues 205 to 234 of SEQ ID NO:9).

For example, a modified FAE1 coding sequence can include a single 'T' can be inserted four base-pairs upstream from the PAM in a WT pennycress FAE1 coding sequence (see, e.g., FIG. 7). A representative modified pennycress FAE1 coding sequence having a loss-of-function single 'T' base-pair insertion is as follows (SEQ ID NO:7):

```
ATGACGTCCGTTAACGTTAAGCTCCTTTACCATTACGTCATCACCAACTT

TTTCAACCTTTGCTTCTTCCCGTTAGCGGCGATCGTTGCCGGAAAAGCCT

CTCGGCTTACCACAAACGATCTTCACCACTTCTACTATTCCTATCTCCAA

CACAACCTAATAACCATATCTCTACTCTTTGCCTTCACCGTTTTCGGTTT

GGCTCTCTACATCGTA※ACCCGGCCCAAACCGGTTTACCTCGTTGACCAT

TCCTGCTACCTTCCACCATCGCATCTTAGAAGCAGTATCTCTAAGGTCAT

GGATATCTTCTATCAAGTAAGATTAGCCGATCCTTTACGGAACGCGGCAA

GCGATGATTCGTCCTGGCTTGATTTCTTGAGGAAGATTCAGGAGCGGTCT

GGTCTAGGCGATGAAACCCACGGCCCCGAGGGACTGCTTCAGGTCCCTCC

ACGGAAGACTTTTGCCGCGGCGCGTGAAGAAACAGAGCAAGTGATCATCG

GTGCGCTCGAAAAACTATTCGAGAACACCAAAGTTAACCCTAAAGAGATT

GGTATACTTGTGGTGAACTCAAGCATGTTTAATCCGACTCCTTCGCTCTC

GGCGATGGTTGTTAATACTTTCAAGCTCCGAAGCAACATCAGAAGCTTTA

ATCTTGGAGGAATGGGTTGTAGTGCCGGCGTTATAGCCATTGATCTGGCT

AAGGACTTGTTGCATGTCCATAAAAACACTTATGCTCTTGTGGTGAGCAC

AGAGAACATCACTTACAACATTTATGCTGGTGATAACAGATCCATGATGG

TTTCGAATTGCTTGTTCCGTGTTGGTGGGGCCGCGATTTTGCTCTCCAAC

AAGCCGAGGGACCGGAGACGGTCCAAGTACCAGCTACTTCACACGGTTCG

GACGCATACCGGAGCTGACGACAAGTCTTTCCGATGTGTGCAACAAGAAG

ACGACGAGAGCGGTAAAACCGGGGTGTGTTTGTCCAAGGACATAACCGGT

GTTGCCGGGAGAACTGTTCAGAAAAACATAACAACATTGGGTCCGTTGGT

TCTTCCTTTTAGCGAGAAATTTCTTTTTTTCGTTACCTTCATCGCCAAGA

AACTCTTTAAAGACAAGATCAAACATTACTACGTCCCGGATTTCAAGCTT

GCTATCGACCATTTTTGTATTCATGCCGGAGGCAGAGCCGTGATCGATGT

GCTACAGAAGAACTTAGGTCTATTGCCGATCGATGTGGAGGCATCTAGGT

CAACGTTACATAGATTTGGGAACACTTCGTCTAGCTCAATTTGGTATGAA

TTGGCGTACATAGAGGCAAAAGGAAGGATGAAGAGAGGGAACAAAGTTTG

GCAGATTGCTTTAGGGTCAGGGTTTAAGTGTAATAGTGCGGTTTGGGTGG

CTCTACGCAATGTCAAGGCTTCGACAAATAGTCCTTGGGAACATTGCATT

GATAGATATCCAGATGCAATTGATTCTGATTCGGGTAAGTCAGAGACTCG

TGTCCAAAACGGTCGGTCCTAA
```

A modified pennycress FAE1 coding sequence having a loss-of-function single 'T' base-pair insertion (e.g., SEQ ID NO:7) can result in a premature STOP codon and disruption of the gene. For example, a modified pennycress FAE1 coding sequence having a loss-of-function single 'T' base-pair insertion (e.g., SEQ ID NO:7) can encode a truncated FAE1 polypeptide. A representative truncated pennycress FAE1 polypeptide is as follows (SEQ ID NO:8):

```
MTSVNVKLLYHYVITNFFNLCFFPLAAIVAGKASRLTTNDLHHFYYSYLQ

HNLITISLLFAFTVFGLALYIVNPAQTGLPR
```

In some cases, oilseed plants having low levels of erucic acid described herein can include a deletion (e.g., a single base-pair deletion) relative to the WT pennycress FAE1 coding sequence (e.g., SEQ ID NO:1). The single base-pair deletion can be a deletion of any appropriate nucleotide. For example, a modified FAE1 coding sequence can include a single 'A' deletion located four base-pairs upstream from a PAM sequence in a WT pennycress FAE1 coding sequence (see, e.g., FIG. 7). A representative modified pennycress FAE1 coding sequence having a loss-of-function single 'A' deletion is as follows (SEQ ID NO:9):

```
ATGACGTCCGTTAACGTTAAGCTCCTTTACCATTACGTCATCACCAACTT

TTTCAACCTTTGCTTCTTCCCGTTAGCGGCGATCGTTGCCGGAAAAGCCT

CTCGGCTTACCACAAACGATCTTCACCACTTCTACTATTCCTATCTCCAA

CACAACCTAATAACCATATCTCTACTCTTTGCCTTCACCGTTTTCGGTTT

GGCTCTCTACATCGTACCCGGCCCAAACCGGTTTACCTCGTTGACCATTC

CTGCTACCTTCCACCATCGCATCTTAGAAGCAGTATCTCTAAGGTCATGG

ATATCTTCTATCAAGTAAGATTAGCCGATCCTTTACGGAACGCGGCAAGC

GATGATTCGTCCTGGCTTGATTTCTTGAGGAAGATTCAGGAGCGGTCTGG
```

TCTAGGCGATGAAACCCACGGCCCCGAGGGACTGCTTCAGGTCCCTCCAC

GGAAGACTTTTGCCGCGGCGCGTGAAGAAACAGAGCAAGTGATCATCGGT

GCGCTCGAAAAACTATTCGAGAACACCAAAGTTAACCCTAAAGAGATTGG

TATACTTGTGGTGAACTCAAGCATGTTTAATCCGACTCCTTCGCTCTCGG

CGATGGTTGTTAATACTTTCAAGCTCCGAAGCAACATCAGAAGCTTTAAT

CTTGGAGGAATGGGTTGTAGTGCCGGCGTTATAGCCATTGATCTGGCTAA

GGACTTGTTGCATGTCCATAAAAACACTTATGCTCTTGTGGTGAGCACAG

AGAACATCACTTACAACATTTATGCTGGTGATAACAGATCCATGATGGTT

TCGAATTGCTTGTTCCGTGTTGGTGGGGCCGCGATTTTGCTCTCCAACAA

GCCGAGGGACCGGAGACGGTCCAAGTACCAGCTACTTCACACGGTTCGGA

CGCATACCGGAGCTGACGACAAGTCTTTCCGATGTGTGCAACAAGAAGAC

GACGAGAGCGGTAAAACCGGGGTGTGTTTGTCCAAGGACATAACCGGTGT

TGCCGGGAGAACTGTTCAGAAAAACATAACAACATTGGGTCCGTTGGTTC

TTCCTTTTAGCGAGAAATTTCTTTTTTTCGTTACCTTCATCGCCAAGAAA

CTCTTTAAAGACAAGATCAAACATTACTACGTCCCGGATTTCAAGCTTGC

TATCGACCATTTTTGTATTCATGCCGGAGGCAGAGCCGTGATCGATGTGC

TACAGAAGAACTTAGGTCTATTGCCGATCGATGTGGAGGCATCTAGGTCA

ACGTTACATAGATTTGGGAACACTTCGTCTAGCTCAATTTGGTATGAATT

GGCGTACATAGAGGCAAAAGGAAGGATGAAGAGAGGGAACAAAGTTTGGC

AGATTGCTTTAGGGTCAGGGTTTAAGTGTAATAGTGCGGTTTGGGTGGCT

CTACGCAATGTCAAGGCTTCGACAAATAGTCCTTGGGAACATTGCATTGA

TAGATATCCAGATGCAATTGATTCTGATTCGGGTAAGTCAGAGACTCGTG

TCCAAAACGGTCGGTCCTAA

A modified pennycress FAE1 coding sequence having a loss-of-function single base-pair deletion (e.g., SEQ ID NO:9) can result in a premature STOP codon and disruption of the gene. For example, a modified pennycress FAE1 coding sequence having a loss-of-function 'A' deletion (e.g., SEQ ID NO:9) can encode a truncated FAE1 polypeptide. A representative truncated pennycress FAE1 polypeptide is as follows (SEQ ID NO:10):

MTSVNVKLLYHYVITNFFNLCFFPLAAIVAGKASRLTTNDLHHFYYSYLQ

HNLITISLLFAFTVFGLALYIPGPNRFTSLTIPATFHHRILEAVSLRSWI

SSIK

In some cases, oilseed plants having low levels of erucic acid described herein can include a substitution (e.g., a single base-pair insertion) relative to the WT pennycress FAE1 coding sequence (e.g., SEQ ID NO:1). The single base-pair substitution can be a substitution of any appropriate nucleotide. For example, a modified FAE1 coding sequence can include an C to T substitution at residue 1018 in a WT pennycress FAE1 coding sequence (e.g., SEQ ID NO:1). A representative modified pennycress FAE1 coding sequence having a loss-of-function C to T substitution is as follows (SEQ ID NO:11):

ATGACGTCCGTTAACGTTAAGCTCCTTTACCATTACGTCATCACCAACTT

TTTCAACCTTTGCTTCTTCCCGTTAGCGGCGATCGTTGCCGGAAAAGCCT

CTCGGCTTACCACAAACGATCTTCACCACTTCTACTATTCCTATCTCCAA

CACAACCTAATAACCATATCTCTACTCTTTGCCTTCACCGTTTTCGGTTT

GGCTCTCTACATCGTAACCCGGCCCAAACCGGTTTACCTCGTTGACCATT

CCTGCTACCTTCCACCATCGCATCTTAGAAGCAGTATCTCTAAGGTCATG

GATATCTTCTATCAAGTAAGATTAGCCGATCCTTTACGGAACGCGGCAAG

CGATGATTCGTCCTGGCTTGATTTCTTGAGGAAGATTCAGGAGCGGTCTG

GTCTAGGCGATGAAACCCACGGCCCCGAGGGACTGCTTCAGGTCCCTCCA

CGGAAGACTTTTGCCGCGGCGCGTGAAGAAACAGAGCAAGTGATCATCGG

TGCGCTCGAAAAACTATTCGAGAACACCAAAGTTAACCCTAAAGAGATTG

GTATACTTGTGGTGAACTCAAGCATGTTTAATCCGACTCCTTCGCTCTCG

GCGATGGTTGTTAATACTTTCAAGCTCCGAAGCAACATCAGAAGCTTTAA

TCTTGGAGGAATGGGTTGTAGTGCCGGCGTTATAGCCATTGATCTGGCTA

AGGACTTGTTGCATGTCCATAAAAACACTTATGCTCTTGTGGTGAGCACA

GAGAACATCACTTACAACATTTATGCTGGTGATAACAGATCCATGATGGT

TTCGAATTGCTTGTTCCGTGTTGGTGGGGCCGCGATTTTGCTCTCCAACA

AGCCGAGGGACCGGAGACGGTCCAAGTACCAGCTACTTCACACGGTTCGG

ACGCATACCGGAGCTGACGACAAGTCTTTCCGATGTGTGCAACAAGAAGA

CGACGAGAGCGGTAAAACCGGGGTGTGTTTGTCCAAGGACATAACCGGTG

TTGCCGGGAGAACTGTTCAGAAAAACATAACAACATTGGGTCCGTTGGTT

CTTCCTTTTAGCGAGAAATTTCTTTTTTTCGTTACCTTCATCGCCAAGAA

ACTCTTTAAAGACAAGATCAAACATTACTACGTCCCGGATTTCAAGCTTG

CTATCGACCATTTTTGTATTCATGCCGGAGGCAGAGCCGTGATCGATGTG

CTACAGAAGAACTTAGGTCTATTGCCGATCGATGTGGAGGCATCTAGGTC

AACGTTACATAGATTTGGGAACACTTCGTCTAGCTCAATTTGGTATGAAT

TGGCGTACATAGAGGCAAAAGGAAGGATGAAGAGAGGGAACAAAGTTTGG

CAGATTGCTTTAGGGTCAGGGTTTAAGTGTAATAGTGCGGTTTGGGTGGC

TCTACGCAATGTCAAGGCTTCGACAAATAGTCCTTGGGAACATTGCATTG

ATAGATATCCAGATGCAATTGATTCTGATTCGGGTAAGTCAGAGACTCGT

GTCCAAAACGGTCGGTCCTAA

A modified pennycress FAE1 coding sequence having a C to T substitution at residue 1018 in a WT pennycress FAE1 coding sequence (e.g., SEQ ID NO:11) can result in a premature STOP codon and disruption of the gene. For example, a modified pennycress FAE1 coding sequence having a C to T substitution at residue 1018 in a WT pennycress FAE1 coding sequence (e.g., SEQ ID NO:11) can encode a truncated FAE1 polypeptide. A representative truncated pennycress FAE1 polypeptide is as follows (SEQ ID NO:12):

MTSVNVKLLYHYVITNFFNLCFFPLAAIVAGKASRLTTNDLHHFYYSYLQ

HNLITISLLFAFTVFGLALYIVTRPKPVYLVDHSCYLPPSHLRSSISKVM

-continued
DIFYQVRLADP-LRNAASDDSSWLDFLRKIQERSGLGDETHGPEGLLQVP

PRKTFAAAREETEQVIIGALEKLFENTKVNPKEIGILVVNSSMFNPTPSL

SAMVVNTFKLRSNIRSFNLGGMGCSAGVIAIDLAKDLLHVHKNTYALVVS

TENITYNIYAGDNRSMMVSNCLFRVGGAAILLSNKPRDRRRSKYQLLHTV

RTHTGADDKSFRCVQQEDDESGKTGVCLSKDITGVAGRTV

For example, a modified FAE1 coding sequence can include a G to A substitution at residue 1349 in a WT pennycress FAE1 coding sequence (e.g., SEQ ID NO:1). A representative modified pennycress FAE1 coding sequence having a loss-of-function G to A substitution is as follows (SEQ ID NO:13):

ATGACGTCCGTTAACGTTAAGCTCCTTTACCATTACGTCATCACCAACTT

TTTCAACCTTTGCTTCTTCCCGTTAGCGGCGATCGTTGCCGGAAAAGCCT

CTCGGCTTACCACAAACGATCTTCACCACTTCTACTATTCCTATCTCCAA

CACAACCTAATAACCATATCTCTACTCTTTGCCTTCACCGTTTTCGGTTT

GGCTCTCTACATCGTAACCCGGCCCAAACCGGTTTACCTCGTTGACCATT

CCTGCTACCTTCCACCATCGCATCTTAGAAGCAGTATCTCTAAGGTCATG

GATATCTTCTATCAAGTAAGATTAGCCGATCCTTTACGGAACGCGGCAAG

CGATGATTCGTCCTGGCTTGATTTCTTGAGGAAGATTCAGGAGCGGTCTG

GTCTAGGCGATGAAACCCACGGCCCCGAGGGACTGCTTCAGGTCCCTCCA

CGGAAGACTTTTGCCGCGGCGCGTGAAGAAACAGAGCAAGTGATCATCGG

TGCGCTCGAAAAACTATTCGAGAACACCAAAGTTAACCCTAAAGAGATTG

GTATACTTGTGGTGAACTCAAGCATGTTTAATCCGACTCCTTCGCTCTCG

GCGATGGTTGTTAATACTTTCAAGCTCCGAAGCAACATCAGAAGCTTTAA

TCTTGGAGGAATGGGTTGTAGTGCCGGCGTTATAGCCATTGATCTGGCTA

AGGACTTGTTGCATGTCCATAAAAACACTTATGCTCTTGTGGTGAGCACA

GAGAACATCACTTACAACATTTATGCTGGTGATAACAGATCCATGATGGT

TTCGAATTGCTTGTTCCGTGTTGGTGGGGCCGCGATTTTGCTCTCCAACA

AGCCGAGGGACCGGAGACGGTCCAAGTACCAGCTACTTCACACGGTTCGG

ACGCATACCGGAGCTGACGACAAGTCTTTCCGATGTGTGCAACAAGAAGA

CGACGAGAGCGGTAAAACCGGGGTGTGTTTGTCCAAGGACATAACCGGTG

TTGCCGGGAGAACTGTTCAGAAAAACATAACAACATTGGGTCCGTTGGTT

CTTCCTTTTAGCGAGAAATTTCTTTTTTTCGTTACCTTCATCGCCAAGAA

ACTCTTTAAAGACAAGATCAAACATTACTACGTCCCGGATTTCAAGCTTG

CTATCGACCATTTTTGTATTCATGCCGGAGGCAGAGCCGTGATCGATGTG

CTACAGAAGAACTTAGGTCTATTGCCGATCGATGTGGAGGCATCTAGGTC

AACGTTACATAGATTTGGGAACACTTCGTCTAGCTCAATTTGGTATGAAT

TGGCGTACATAGAGGCAAAAGGAAGGATGAAGAGAGGGAACAAAGTTAG

CAGATTGCTTTAGGGTCAGGGTTTAAGTGTAATAGTGCGGTTTGGGTGGC

TCTACGCAATGTCAAGGCTTCGACAAATAGTCCTTGGGAACATTGCATTG

ATAGATATCCAGATGCAATTGATTCTGATTCGGGTAAGTCAGAGACTCGT

GTCCAAAACGGTCGGTCCTAA

A modified pennycress FAE1 coding sequence having a G to A substitution at residue 1349 in a WT pennycress FAE1 coding sequence (e.g., SEQ ID NO:13) can result in a premature STOP codon and disruption of the gene. For example, a modified pennycress FAE1 coding sequence having a G to A substitution at residue 1349 in a WT pennycress FAE1 coding sequence (e.g., SEQ ID NO:13) can encode a truncated FAE1 polypeptide. A representative truncated pennycress FAE1 polypeptide is as follows (SEQ ID NO:14):

MTSVNVKLLYHYVITNFFNLCFFPLAAIVAGKASRLTTNDLHHFYYSYLQ

HNLITISLLFAFTVFGLALYIVTRPKPVYLVDHSCYLPPSHLRSSISKVM

DIFYQVRLADP-LRNAASDDSSWLDFLRKIQERSGLGDETHGPEGLLQVP

PRKTFAAAREETEQVIIGALEKLFENTKVNPKEIGILVVNSSMFNPTPSL

SAMVVNTFKLRSNIRSFNLGGMGCSAGVIAIDLAKDLLHVHKNTYALVVS

TENITYNIYAGDNRSMMVSNCLFRVGGAAILLSNKPRDRRRSKYQLLHTV

RTHTGADDKSFRCVQQEDDESGKTGVCLSKDITGVAGRTVQKNITTLGPL

VLPFSEKFLFFVTFIAKKLFKDKIKHYYVPDFKLAIDHFCIHAGGRAVID

VLQKNLGLLPIDVEASRSTLHRFGNTSSSSIWYELAYIEAKGRMKRGNKV

Any appropriate method can be used to introduce one or more modifications into an FAE1 gene (e.g., in an FAE1 coding sequence) to produce oilseed plants having low levels of erucic acid as described herein. Examples of methods for modifying an FAE1 coding sequence include, without limitation, genome editing (e.g., genome editing with engineered nucleases (GEEN)) and introduction of a transgene (e.g., gene transfer). For example, genome editing can be used to produce oilseed plants having low levels of erucic acid. Genome editing can insert, replace, or remove DNA from a genome using one or more site-specific nucleases (SSN) and, in some cases, a repair template (RT). Nucleases can be targeted to a specific position in the genome, where their action can introduce a particular modification to the endogenous sequences. For example, a SSN can introduce a targeted double-strand break (DSB) in the genome, such that cellular DSB repair mechanisms incorporate a RT into the genome in a configuration that produces heritable genome edits (e.g., a loss-of-function modification in an FAE1 coding sequence) in the cell, in a plant regenerated from the cell, and in any progeny of the regenerated plant. Nucleases useful for genome editing include, without limitation, CRISPR-associated (Cas) nucleases, zinc finger nucleases (ZFNs), transcription activator-like effector (TALE) nucleases, and homing endonucleases (HE; also referred to as meganucleases).

In some cases, a CRISPR/Cas system can be used to introduce one or more loss-of-function modifications described herein into the coding sequence of a gene involved in erucic acid biosynthesis (e.g., FAE1). For example, a CRISPR/Cas vector can include at least one guide sequence specific to a pennycress FAE1 sequence (see, e.g., FIG. 7 and Example 2) upstream of a PAM. A Cas enzyme will bind to and cleave within a target sequence (e.g., a nucleic acid sequence specific to FAE1) only if the target site is followed by a PAM sequence. For example, the canonical PAM is the sequence 5'-NGG-3', where N is any nucleotide followed by two guanine (G) nucleotides. In some cases, the canonical PAM can be a 5'-CGG-3' sequence. Thus, in some cases, a guide sequence useful for introducing one or more loss-of-function modifications described herein into an FAE1 coding sequence can include a nucleic acid sequence specific to FAE1. A representative guide sequence that can be used to direct a Cas nuclease to the FAE1 gene is as follows: TGGCTCTCTACATCGTAACC; SEQ ID NO:15.

The Cas component of a CRISP/Cas system described herein can be any appropriate Cas nuclease. Examples of Cas nucleases include, without limitation, Cas1, Cas2, Cas3, Cas9, Cas10, and Cpf1. In some cases, the Cas component of a CRISPR/Cas system designed to introduce one or more loss-of-function modifications described herein into an FAE1 coding sequence can be a Cas9 nuclease. For example, the Cas9 nuclease of a CRISPR/Cas9 system described herein can be a *Streptococcus pyogenes* Cas9 (spCas9). One example of an spCas9 is described in, for example, Fauser et al., 2014 *The Plant Journal* 79:348-359.

The oilseed plants having low levels of erucic acid as described herein also can include low levels of glucosinolates. For example, the oilseed plants having low levels of erucic acid as described herein also can include one or more modifications in a gene that encodes a polypeptide involved in glucosinolate biosynthesis. Polypeptides involved in glucosinolate biosynthesis include, without limitation, HAG1, GTR1, GTR2, REF2, AOP2, MAM1, BCAT4, and FMOGS.

The oilseed plants having low levels of erucic acid as described herein also can exhibit decreased pod strength (e.g., can be shatterproof). For example, the oilseed plants having low levels of erucic acid as described herein also can include one or more modifications in a gene that encodes a polypeptide involved in pod strength. Polypeptides involved in pod strength include, without limitation, SHP1, SHP2, IND, ALC, RPL, FUL, ADPG2, and PDH1.

The genome editing reagents described herein can be introduced into an oilseed plant by any appropriate method. In some cases, nucleic acids encoding the genome editing reagents can be introduced into a plant cell using *Agrobacterium* or *Ensifer* mediated transformation, particle bombardment, liposome delivery, nanoparticle delivery, electroporation, polyethylene glycol (PEG) transformation, or any other method suitable for introducing a nucleic acid into a plant cell. In some cases, the SSN or other expressed gene editing reagents can be delivered as RNAs or as proteins to a plant cell and the RT, if one is used, can be delivered as DNA.

The oilseed plants having low levels of erucic acid as described herein can be identified by, for example, an NIR analyzer (e.g., as described in the Examples).

The invention will be further described in the following examples, which do not limit the scope of the invention described in the claims.

EXAMPLES

Example 1

Creation of Low Erucic Acid Pennycress by EMS Mutagenesis

Mutagenesis

Seeds derived from pennycress accession MN106 were collected as described elsewhere (see, e.g., Dorn et al., 2013 *The Plant Journal*, 75:1028-38), and were treated with 180 ml 0.2% ethyl methanesulfonate (EMS) in a chemical flow hood. The solution and seeds were kept mixed on a rotating platform for 14 hours at room temperature. The seeds were thereafter extensively rinsed with distilled water to remove all traces of the EMS. The seeds were then dried for 24 hours on filter paper in a chemical flow hood. These seeds were considered to be the progenitors of the M1 generation of plants.

Growing of the M1 Generation

Figure 3:
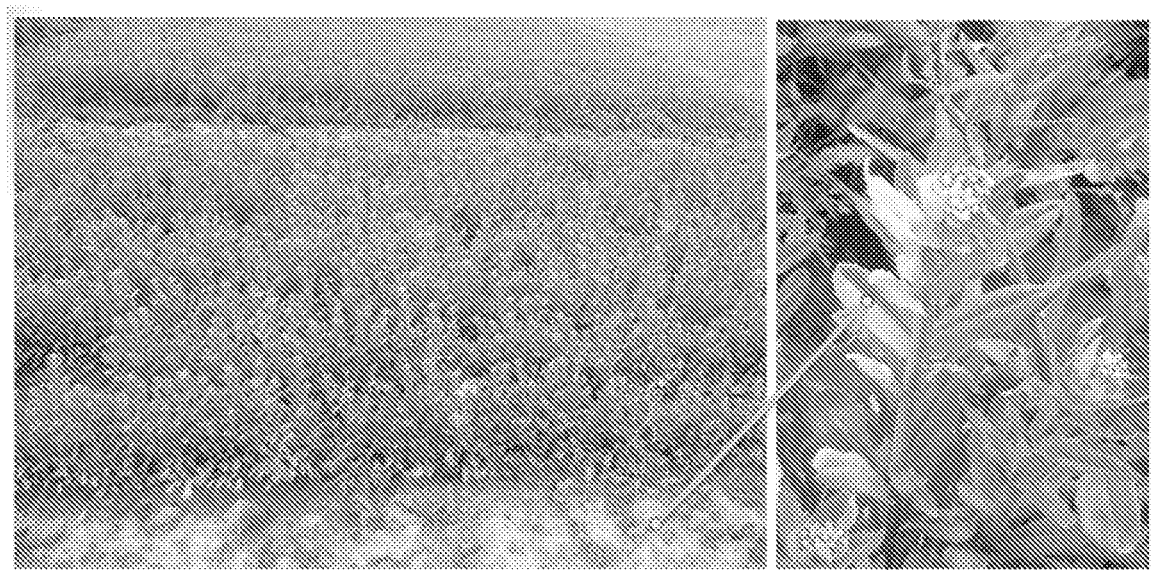
FIG. 3 contains photographs of ethyl methanesulfonate (EMS)-mutagenized $M_1$-generation (M1) plants in the field. On the left is a plot of the mutagenized M1 plants. On the right is an M1 plant showing an albino sector (arrow).

The mutagenized seeds were sowed into small field plots. These plots were allowed to grow over winter. The following spring abundant albino sectors were noted on the flowering plants (FIG. 3). Such sectoring is the hallmark of a successful mutagenesis.

Collection and Growing of M2 Seeds

Figure 4:
FIG. 4 contains a photograph of the growth of $M_2$-generation (M2) pools of seeds in individual rows. The photographed field contained over 50,000 plants.
Figure 5:
FIG. 5 contains a photograph of a field containing mature mutagenized M2 plants.

Seeds were collected from mature M1 plants. M2 seeds from batches of 10 M1 plants were pooled together. Each pool was sowed in a field into an individual row. Robust growth was noted in the fall (FIG. 4). During the following spring and early summer, M3 seeds were collected from mature M2 individual plants (FIG. 5) and stored individual packets.

NIR Spectral Analysis to Identify Lines with Reduced Erucic Acid

M3 seeds from each packet were scanned using a Perten DA7250 NIR spectroscopy analyzer to assess the quality of oil seeds as described elsewhere (Sidhu et al., 2014 *Applied Engineering in Agriculture*, 30:69-76; Golebiowski et al, 2005 *Journal of near Infrared Spectroscopy*, 13:255-264; Riu et al., 2006 *Spectroscopy and Spectral Analysis*, 26:2190-2192; and Xin et al., 2014 *Journal of Agricultural and Food Chemistry*, 62:7977-7988). These analyses captured information related to the approximate levels of, for example, the main fatty acids found in pennycress (eicosenoic, steric, palmitic, oleic, linoleic, linolenic, and erucic acids. None of the lines showed a complete reduction in erucic acid in the fall, but an intermediate reduction in erucic acid in several lines were observed the following spring. An example analysis is show below.

| SampleID | Eicosenoate20:1 | Ercuate22:1 | Linoleate18:2 | Linolenate18:3 | Oleicacid18:0 | Palmitate | Stearate |
|---|---|---|---|---|---|---|---|
| E3814 | 0.79 | 9.83 | 31.67 | 12.13 | 70.47 | 4.5 | 1.5 |

Figure 6:
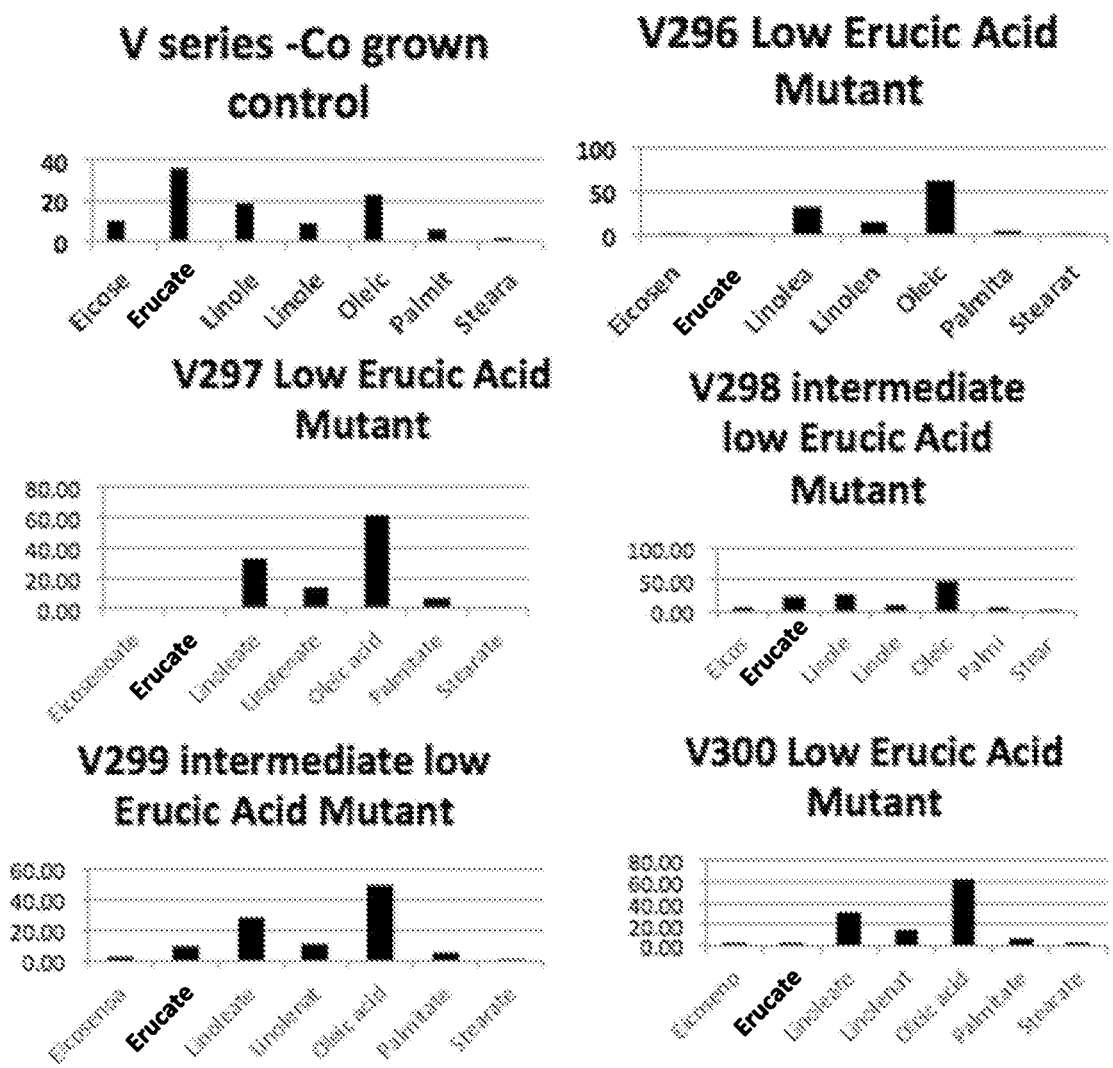
FIG. 6 contains near infrared (NIR) spectroscopy-derived fatty acid profiles for individual plants derived from the parental E3814 pennycress line. A co-grown control also is shown. V296, V297, and V300 seed oil contains undetectable levels of erucic acid, whereas V298 and V299 show levels similar to E3814.

M3 seeds from candidate lines were sowed into small plots in a field during the second week of March. These M4 plants matured in July and M4 seeds were collected from five individual M3 plants in each plot. During the next fall, these seeds were scanned with the same NIR instrument as before, and a family of individuals segregating for a loss of erucic acid, designated V296-V300 were identified (FIG. 6).

The NIR results were confirmed using gas chromatography—mass spectrometry (GC-MS). Results are shown below in Table 1. As shown for the NIR analysis V296, V297, and V300 all lacked erucic acid (22:1).

The results are consistent with a mutation in the *Fatty Acid Elongase* 1 (FAE1) gene.

TABLE 1

GC-MS analysis of fatty acids in low erucic acid mutants and co-grown controls.

| Sample name | 16:0 | 16:1 | 18:0 | 18:1 | 18:2 | 18:3 | 20:0 | 20:1 | 20:2 | 20:3 | 22:0 | 22:1 | 22:2 | 22:3 | 24:1 |
|---|---|---|---|---|---|---|---|---|---|---|---|---|---|---|---|
| V300 | 3.9 | 0.3 | 0.7 | 37.5 | 33.5 | 22.0 | 0.2 | 0.7 | 0.0 | 0.0 | 0.2 | 0.0 | 0.0 | 0.6 | 0.3 |
| V299 | 3.5 | 0.4 | 0.6 | 27.7 | 27.5 | 18.3 | 0.2 | 5.7 | 0.7 | 0.2 | 0.1 | 13.0 | 0.3 | 0.7 | 1.2 |
| V297 | 4.2 | 0.3 | 0.8 | 35.4 | 34.9 | 22.1 | 0.2 | 0.6 | 0.0 | 0.0 | 0.0 | 0.0 | 0.0 | 0.6 | 0.8 |
| V296 | 3.8 | 0.3 | 0.8 | 37.9 | 33.0 | 21.3 | 0.2 | 0.7 | 0.0 | 0.0 | 0.1 | 0.0 | 0.0 | 0.5 | 0.4 |
| Control V091 | 3.4 | 0.5 | 0.4 | 12.4 | 19.7 | 14.1 | 0.2 | 8.7 | 1.5 | 0.4 | 0.2 | 34.8 | 0.7 | 0.4 | 2.6 |
| Control V129 | 3.6 | 0.4 | 0.4 | 15.2 | 19.8 | 14.2 | 0.2 | 9.7 | 1.4 | 0.4 | 0.2 | 31.1 | 0.5 | 0.5 | 2.5 |
| Control V193 | 3.8 | 0.5 | 0.4 | 14.2 | 20.1 | 14.9 | 0.2 | 9.4 | 1.4 | 0.4 | 0.1 | 31.1 | 0.6 | 0.5 | 2.4 |
| Control V338 | 3.8 | 0.5 | 0.5 | 13.1 | 20.0 | 13.2 | 0.3 | 9.3 | 1.5 | 0.4 | 0.3 | 33.0 | 0.6 | 0.4 | 3.2 |
| Control V057 | 3.2 | 0.5 | 0.4 | 12.1 | 20.6 | 12.8 | 0.2 | 10.0 | 1.6 | 0.3 | 0.2 | 34.4 | 0.6 | 0.4 | 2.7 |

The parent mutant from this screen is subsequently referred to as UMN Ta fae1-1 (see below).

Figure 11:
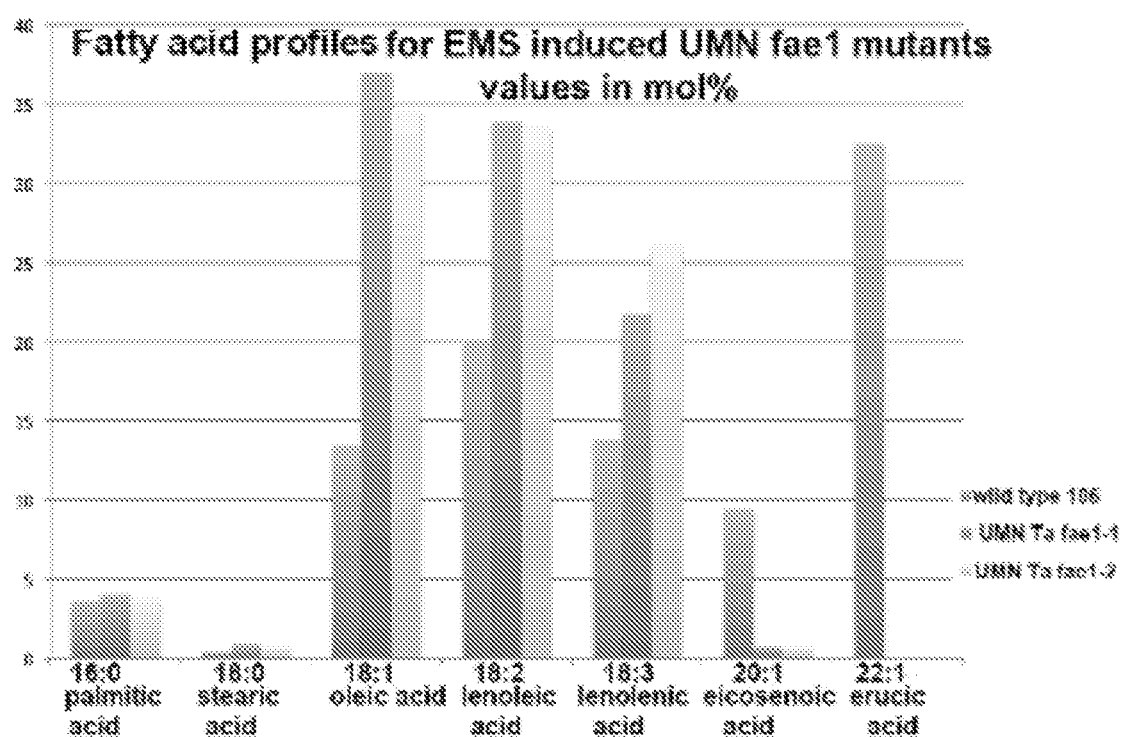
FIG. 11 contains near infrared (NIR) spectroscopy-derived fatty acid profiles for two independent EMS induced fae1-1 lines.

In other cases, the NIR analyses identifies candidate lines with very low in erucic acid (e.g., a line referred to as UMN Ta fae1-2). Shown in FIG. 11 is a graph comparing the fatty acid profiles of two independent EMS induced fae1-1.

Example 2

Creation of Low Erucic Acid Pennycress by Direct Targeting of FAE1 with CRISPR/Cas9

Construction of the Thlaspi arvense (Pennycress) FAE1 Gene-Specific CRISPR-Cas9 Vector.

The constructs and cloning procedures used for generation of the Thlaspi arvense (pennycress) FAE1-specific CRISPR-Cas9 construct were as described elsewhere (see, e.g., Fauser et al., 2014 The Plant Journal 79:348-359). The plant selectable marker in the pDe-Cas9 binary vector (formerly basta) was swapped for hygromycin resistance (the Hygromycin phosphotransferase (hpt) gene) to create a pDe-Cas9_Hyg vector.

The following oligos were annealed to create a 20-mer protospacer specific to the pennycress FAE1 sequence:

```
PennyFAE1_CRISPR_FWD:
                                  (SEQ ID NO: 16)
5' ATTGTGGCTCTCTACATCGTAACC 3';
and PennyFAE1_CRISPR_REV:
                                  (SEQ ID NO:17)
5' AAACGGTTACGATGTAGAGAGCCA 3'.
```

Vector Transformation into Agrobacterium tumefaciens Strain GV3101.

The pDe-Cas9_Hyg vector containing the pennycress FAE1 sequence-specific protospacer was transformed into Agrobacterium tumefaciens strain GV3101 using the freeze/thaw method as described elsewhere (see, e.g., indiana.edu/~pikweb/Protocols%20page.html). The transformation product was plated on 1% agar Luria broth (LB) plates with gentamicin (50 µg/ml), rifampicin (50 µg/ml), and spectinomycin (75 µg/ml). Single colonies were selected after two days of growth at 28° C.

Plant Transformation (Pennycress Floral Dip).

On Day 1, Agrobacterium were inoculated with 5 mL of LB+5 uL appropriate antibiotics (e.g., rifampicin (50 µg/ml), spectinomycin (75 µg/ml), and/or gentamicin (50 µg/ml)), and the inoculated Agrobacterium were allowed to grow with shaking overnight at 28° C. On Day 2, in the early morning, the Agrobacterium culture from Day 1, was inoculated with 25 mL of Luria Broth+25 uL appropriate antibiotics (e.g., rifampicin (50 µg/ml), spectinomycin (75 µg/ml), and/or gentamicin (50 µg/ml)), and the inoculated Agrobacterium were allowed to grow with shaking overnight at 28° C. On Day 2, in the late afternoon, the Agrobacterium culture from earlier on Day 2, 25 mL of the culture was inoculated with 250 mL of Luria Broth+250 uL appropriate antibiotic(s) (e.g., rifampicin (50 µg/ml), spectinomycin (75 µg/ml), and/or gentamicin (50 µg/ml)), and the inoculated Agrobacterium were allowed to grow with shaking overnight at 28° C. On Day 3, when the culture had grown to an $OD_{600}$ of ~1 (or when it looked thick and silky), the Agrobacterium culture was decanted into large centrifuge tubes (all evenly weighted with analytical balance), and spun at 3,500 RPM at room temperature for 10 minutes to pellet cells. The supernatant was decanted. The pelleted cells were resuspended in a solution of 5% sucrose 0.02% Silwet L-77. The resuspended Agrobacterium cells were poured into clean beakers and placed in a vacuum chamber. Newly flowering inflorescences of pennycress were fully submerged into the beakers, and subjected to a pressure of 14.7 PSI for 10 minutes. After racemes of pennycress plants (Spring32 variety) were dipped, they were covered loosely with Saran wrap to maintain humidity and kept in the dark overnight before being uncovered and placed back in the environmental growth chamber.

Screening and Growth Conditions.

Pennycress seeds were surface sterilized by first rinsing in 70% ethanol then a 10-minute incubation in a 30% bleach, 0.05% SDS solution before being rinsed two times with sterile water and plated on selective plates (0.8% agar/one half-strength Murashige and Skoog salts with hygromycin B selection at 40 U ml$^{-1}$). Plates were wrapped in parafilm and kept in an environmental growth chamber at 21° C., 16:8 day/night for 8 days until hygromycin selection was apparent. Surviving hygromycin-resistant seedlings were transplanted into autoclaved Reddiearth soil mix and grown in an environmental growth chamber set to 16 hour days/8 hour nights at 21° C. and 50% humidity.

After three generations post-hygromycin selection, 100 mg leaf tissue of individual plants were crushed in SDS-PAGE sample buffer and 20 uL per sample was loaded into 7.5% polyacrylamide gels and transferred onto a nitrocellulose membrane for western blots. Primary antibody Guide-it Cas9 Polyclonal antibody (Clontech #632607) was used at a 1:1,500 dilution in TBST+5% milk. Secondary α-Rabbit HRP (Thermo #31460) was used at a 1:5,000 dilution in TBST+5% milk. Membranes were exposed after addition of Supersignal chemiluminescent substrate (Thermo #34077).

Individual plants expressing the spCas9 protein were moved forward to DNA extraction and sequencing.
Cetyl Trimethylammonium Bromide (CTAB) Genomic DNA Extraction An extraction buffer was prepared as follows:

| Extraction Buffer (500 ml) | |
| --- | --- |
| 0.35 M sorbitol | 32 g |
| 0.1 M Tris base | 6 g |
| 5 mM EDTA-Na2 | 0.84 g (or EDTA-Na4 1.0 g) |

Sterile water was added to bring the total volume to 500 ml. The buffer was adjusted to pH 7.5 with high concentration HCl.

A lysis buffer was prepared as follows:

| Lysis Buffer (500 ml) | |
| --- | --- |
| 0.2 M Tris-base | 12.1 g |
| 0.05 M EDTA-Na2 | 8.4 g (or EDTA-Na4 10 g) |
| 2 M NaCl | 58.5 g |
| 2% CTAB | 10 g |
| 1% PVP | 5g |

Sterile water was added to bring the total volume to 500 ml.

Equal parts of extraction buffers and lysis buffer were mixed and 10 units per 500 uL of RNAseA (Thermo #EN0531) was added to make a working solution.

Leaf plant tissue was ground in a ball mill. In a tube, the ground tissue was added to 500 uL of the working solution. The mixture was vortexed and then incubated in a 65° C. waterbath for 20 minutes. 500 uL of 24:1 chloroform-isoamyl mixture was added, and the tubes were inverted 6 times. The tubes were spun at 12,000 RPM at 4° C. for 10 minutes. 400 uL of the supernatant was moved to a new tube. 1 mL of cold 95% ETOH was added to the supernatant, and the tubes were inverted 6 times. The tubes were spun at 12,000 RPM for 15 minutes, and the supernatant was discarded. 400 uL of −20° C. 70% ETOH was added to the pellet. The tubes were spun at 12,000 RPM for 2 minutes, and the supernatant was discarded. The DNA pellet was air dried. Once dry, the pellet was resuspended in 200 uL sterile water. DNA concentrations were analyzed using a Nanodrop and normalized to 200 ng/ul.

PCR Amplification and Gel Purification of FAE1 Gene

PCR primers used to amplify the entire FAE1 gene from the DNA preps of individual plants are as follows:

```
                                        (SEQ ID NO: 18)
pennyFAE1_OuterF1 5' ACATGCATGTAAAACGTAACGG 3', (SEQ ID NO: 19)
pennyFAE1_OuterR1 5' TGGATTATATCAGGATGTGGCG 3'.
```

PCR was performed using a Phusion (NEB #M0530) polymerase, and the following cycling parameters: 1 cycle of 1 minute at 98° C.; 32 repeated cycles of 98° C. for 10 seconds, 55° C. for 15 seconds, and 72° C. for 2 minutes; followed by 1 cycle of 5 minutes at 72° C.

PCR products were run on a 1% agarose gel. Bands of the expected 1.8 kb size were cut out and DNA was purified using the GeneJET Gel Extraction kit (#K0692)
Sequencing and Sequence Analysis Gel purified FAE1 sequences were sequenced with the primer pennyFAE1_OuterF1 (5' ACATG-CATGTAAAACGTAACGG 3'; SEQ ID NO:18).

Sequences were analyzed using Benchling software.

Figure 8:
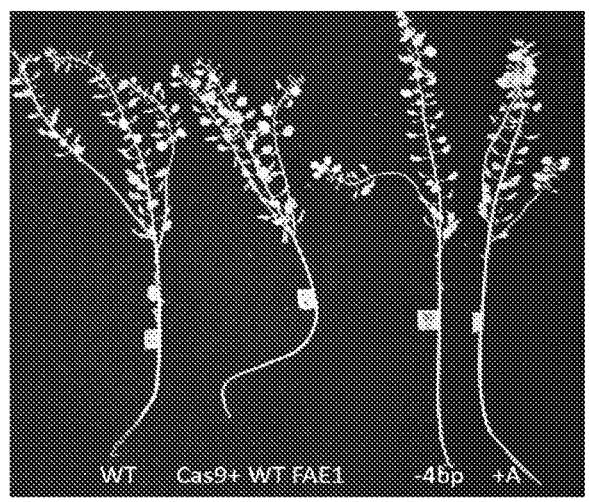
FIGS. 8A to 8C shows that WT plants, control (Cas9+WT FAE1) plant, fae1 homozygous mutant plants having the 4 base-pair deletion (−4 bp) shown in FIG. 7, and fae1 homozygous mutant plants having the single base-pair insertion of an 'A' (+A) shown in FIG. 7, which are phenotypically indistinguishable from one another.
Figure 8:
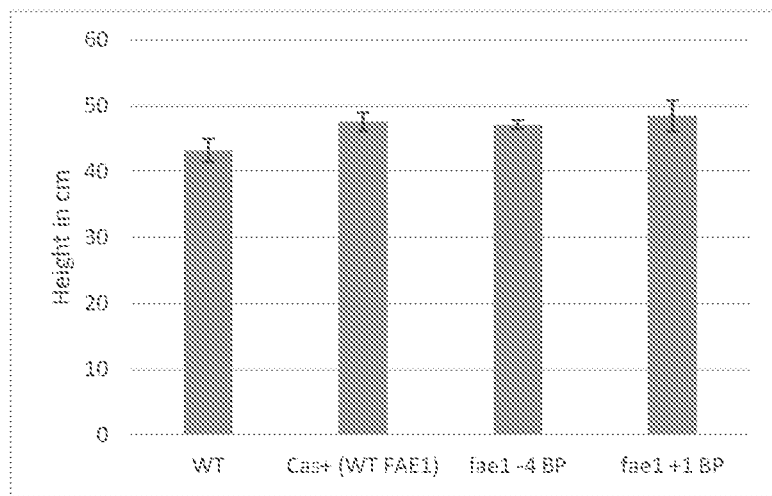
Figure 8:
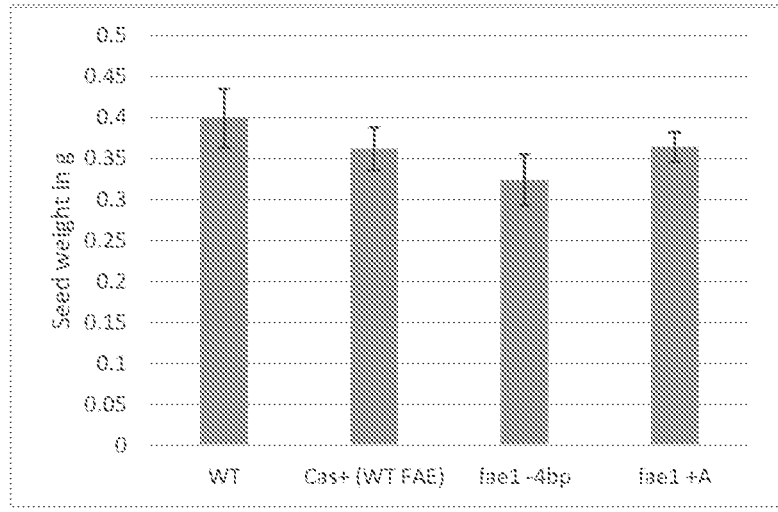

Many unique mutations were found. Some of these mutations include one resulting in a 4 base-pair deletion four base-pairs upstream from the PAM site, one resulting in an additional 'A' (single base-pair insertion) five base-pairs upstream from the PAM site, one resulting in an additional 'T' (single base-pair insertion) four base-pairs upstream from the PAM site, and one resulting in a single base-pair deletion five base-pairs upstream from the PAM site (FIG. 7).
Plant Morphology fae1 mutant plants were phenotypically indistinguishable from wild-type (FIG. 8).
Lipid Analysis Total oil was quantified by gas chromatographic (GC) analysis of fatty acid methyl esters extracted from pennycress seeds described elsewhere (see, e.g., Kim et al., 2015 *Journal of Experimental Botany* 2015:erv225.

Total lipids were extracted for analysis of fatty acid composition using a modified version of a Bligh and Dyer method as described elsewhere (see, e.g., Bligh et al., 1959 *Canadian Journal of Biochemistry and Physiology* 37:911-917).

Figure 9:
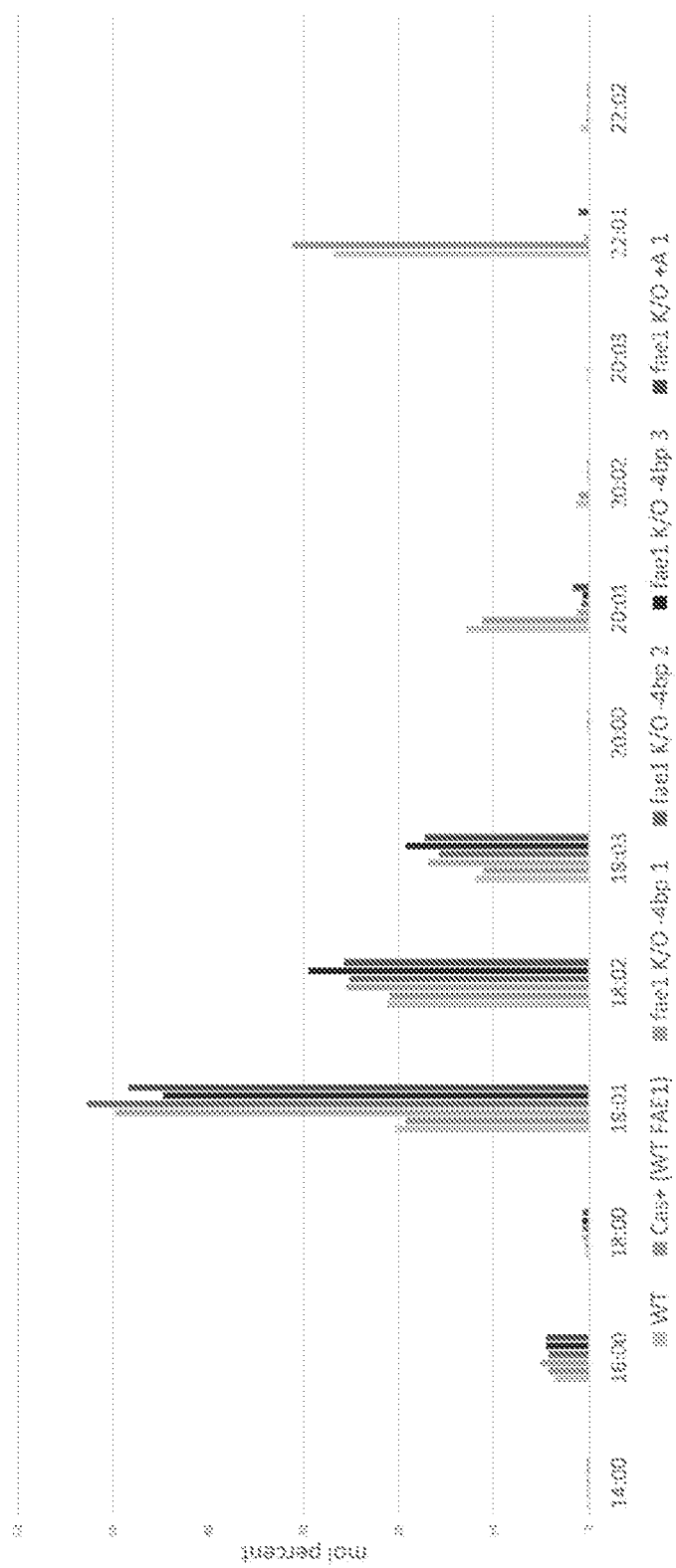
FIG. 9 is a graph showing the seed oil lipid profiles of homozygous fae1 knockout (K/O) pennycress plants having the 4 base-pair deletion (−4 bp) or the single base-pair insertion of an 'A' (+A) as shown in FIG. 7, as compared to WT pennycress plants. Values are in mole percent.

Results of fatty acid analyses are shown below (Table 2) and in FIG. 9.

TABLE 2

GC analysis of fatty acids in FAE1 targeted plants and controls.

| | 14:00 | 16:00 | 18:00 | 18:01 | 18:02 | 18:03 | 20:00 | 20:01 | 20:02 | 20:03 | 22:01 | 22:02 |
| --- | --- | --- | --- | --- | --- | --- | --- | --- | --- | --- | --- | --- |
| WT | 0.2 | 3.6 | 0.4 | 20.3 | 21.2 | 12 | 0 | 13 | 1.4 | 0.2 | 26.8 | 0.9 |
| Cas9+ (WT FAE1) | 0.2 | 4.3 | 0.4 | 19.3 | 21 | 11.1 | 0 | 11.2 | 1 | 0.2 | 31.2 | 0.3 |
| FAE1 K/O −4bp 1 | 0.2 | 5.1 | 0.7 | 49.7 | 25.5 | 16.9 | 0 | 1.2 | 0 | 0 | 0.5 | 0.2 |
| FAE1 K/O −4bp 2 | 0.2 | 4.3 | 0.6 | 52.8 | 25.2 | 15.8 | 0.1 | 0.8 | 0.1 | 0 | 0 | 0.1 |
| FAE1 K/O −4bp 3 | 0.2 | 4.5 | 0.7 | 44.8 | 29.5 | 19.3 | 0.1 | 0.6 | 0.1 | 0 | 0 | 0.1 |
| FAE1 K/O +A 1 | 0.2 | 4.5 | 0.6 | 48.4 | 25.8 | 17.3 | 0.1 | 1.7 | 0.2 | 0 | 1.1 | 0.1 |

* Values in mole percent

Figure 10:
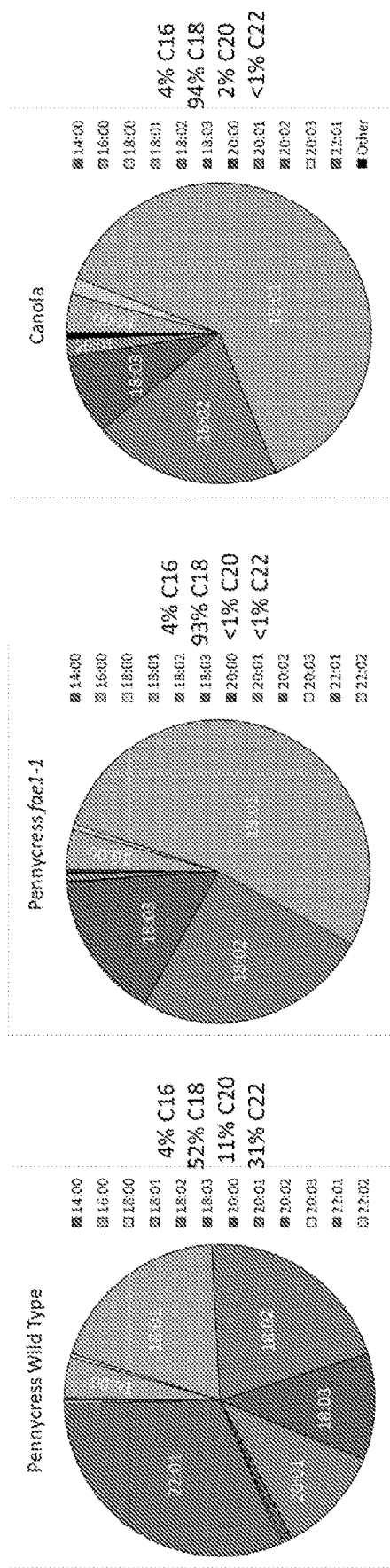
FIG. 10 contains charts showing the seed oil lipid profiles of pennycress WT plants (left), pennycress homozygous fae1 knock out (K/O) plants having the 4 base-pair deletion (middle), and canola plants (right).

Both the four base-pair deletion (−4 bp) and the single insertion (+A) mutations induced by CRISPR-Cas9 in pennycress FAE1 resulted in an abolishment of C20 and C22 fatty acids, and a ~30% increase in C18 fatty acids in pennycress seed oil, producing a 'zero erucic acid' variety akin to canola (FIG. 10). Both mutations were heritable, and the resultant plants were healthy and grew as wild type.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A non-naturally occurring pennycress mutant plant having low levels of erucic acid as compared to a corresponding wild type pennycress plant, said non-naturally occurring pennycress mutant plant comprising: a genome comprising a loss-of-function modification in a coding sequence of a fatty acid elongase 1 (FAE1) gene, wherein the corresponding wild type pennycress plant comprises a wild type FAE1 coding sequence encoding an FAE1 polypeptide having at least 98% amino acid sequence identity to SEQ ID NO:2, wherein said loss-of-function modification is in said wild-type FAE1 coding sequence encoding said FAE1 polypeptide; and wherein said pennycress plant produces seed oil comprising less than 5% erucic acid by weight.

2. The non-naturally occurring pennycress mutant plant of claim 1, wherein said seed oil comprises less than 2% erucic acid by weight.

3. The non-naturally occurring pennycress mutant plant of claim 1, wherein said modified FAE1 coding sequence encodes a truncated FAE1 polypeptide.

4. The non-naturally occurring pennycress mutant plant of claim 1, wherein said seed oil comprises less than 2% eicosenoic acid by weight.

5. The non-naturally occurring pennycress mutant plant of claim 1, wherein said seed oil comprises 25% to 55% oleic acid by weight.

6. The non-naturally occurring pennycress mutant plant of claim 1, wherein said seed oil comprises 20% to 40% linoleic acid by weight.

7. The non-naturally occurring pennycress mutant plant of claim 1, wherein said seed oil comprises 13% to 30% linolenic acid by weight.

8. A non-naturally occurring pennycress mutant seed produced by the non-naturally occurring pennycress mutant plant of claim 1, wherein said mutant seed comprises said genome comprising said loss-of-function modification; and wherein said mutant seed contains oil comprising less than 5% erucic acid by weight.

9. The non-naturally occurring pennycress mutant seed of claim 8, wherein the seed oil comprises less than 2% eicosenoic acid by weight.

10. The non-naturally occurring pennycress mutant seed of claim 8, wherein the seed oil comprises 25% to 55% oleic acid by weight.

11. The non-naturally occurring pennycress mutant seed of claim 8, wherein the seed oil comprises 20% to 40% linoleic acid by weight.

12. The non-naturally occurring pennycress mutant seed of claim 8, wherein the seed oil comprises 13% to 30% linolenic acid by weight.

13. The non-naturally occurring pennycress mutant plant of claim 1, wherein said seed oil lacks erucic acid.

14. The non-naturally occurring pennycress mutant plant of claim 1, wherein said loss-of-function modification is introduced into said FAE1 coding sequence by mutagenesis.

15. The non-naturally occurring pennycress mutant plant of claim 1, wherein said loss-of-function modification is introduced into said FAE1 coding sequence by genome editing.

16. The pennycress seed of claim 8, wherein said seed oil lacks erucic acid.

* * * * *